(12) United States Patent
Chao et al.

(10) Patent No.: US 11,123,424 B2
(45) Date of Patent: Sep. 21, 2021

(54) BACULOVIRUS AND COMPOSITION FOR DETECTION AND PREVENTING OF PORCINE EPIDEMIC DIARRHEA VIRUS INFECTION

(71) Applicant: Academia Sinica, Taipei (TW)

(72) Inventors: Yu-Chan Chao, Taipei (TW); Wei-Ting Hsu, Taipei (TW); Hui-Wen Chang, Taipei (TW); Chia-Yu Chang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/450,810

(22) Filed: Jun. 24, 2019

(65) Prior Publication Data

US 2019/0388535 A1 Dec. 26, 2019

Related U.S. Application Data

(60) Provisional application No. 62/689,427, filed on Jun. 25, 2018.

(51) Int. Cl.
| | |
|---|---|
| *C12N 7/00* | (2006.01) |
| *A61K 39/215* | (2006.01) |
| *A61K 39/12* | (2006.01) |
| *A61K 39/225* | (2006.01) |
| *C07K 14/01* | (2006.01) |
| *G01N 33/569* | (2006.01) |
| *C12N 15/86* | (2006.01) |
| *A61K 39/00* | (2006.01) |

(52) U.S. Cl.
CPC ............ *A61K 39/225* (2013.01); *C07K 14/01* (2013.01); *C12N 15/86* (2013.01); *G01N 33/569* (2013.01); *A61K 2039/552* (2013.01); *A61K 2039/55544* (2013.01)

(58) Field of Classification Search
None
See application file for complete search history.

(56) References Cited

U.S. PATENT DOCUMENTS

| 7,527,967 | B2 * | 5/2009 | Chao ...................... | C12N 15/86 435/320.1 |
| 2015/0328307 | A1 * | 11/2015 | Lawrence ................ | C12N 7/00 424/186.1 |
| 2016/0238601 | A1 * | 8/2016 | Baric .................... | C07K 14/005 |
| 2016/0339097 | A1 * | 11/2016 | Kim ...................... | C07K 14/005 |

* cited by examiner

*Primary Examiner* — M Franco G Salvoza
(74) *Attorney, Agent, or Firm* — Birch, Stewart, Kolasch & Birch, LLP

(57) ABSTRACT

A baculovirus displaying a porcine epidemic diarrhea virus S protein or S1 domain thereof is provided for preventing porcine epidemic diarrhea virus infection.

8 Claims, 10 Drawing Sheets
Specification includes a Sequence Listing.

BACULOVIRUS AND COMPOSITION FOR DETECTION AND PREVENTING OF PORCINE EPIDEMIC DIARRHEA VIRUS INFECTION

RELATED APPLICATIONS

The present application claims priority of U.S. provisional application having Ser. No. 62/689,427 filed Jun. 25, 2018, which is hereby incorporated by reference herein for all purposes.

TECHNICAL FIELD

The present disclosure relates to a baculovirus; particularly to display proteins used for detecting and preventing of pigs from porcine epidemic diarrhea virus infection.

DESCRIPTION OF RELATED ART

Porcine epidemic diarrhea (PED) is a highly contagious swine disease characterized by acute watery diarrhea and vomiting in piglets. The PED was first identified in 1970s in Europe and subsequently became an endemic disease with sporadic outbreaks in Asia and Europe. Since late of 2010, high virulent porcine epidemic diarrhea virus (PEDV) emerged and had attacked neonatal piglets in China. In 2013, outbreaks of the high virulent PED were reported in North America and East Asia, including Taiwan, resulting in dramatic economic losses in swine industries.

The commercially available vaccine is a PEDV RNA vaccine, and previous results showed that application of the vaccine could only reduce mortality of piglets by 3%. The second one used killed PEDV viruses, and low viral yield with a titer of 6.6 $\log^{10}$ TCID50/mL is obviously a limitation for broad application of the vaccine. Therefore, a lot of efforts have been paid for developing vaccines for controlling the epidemic of PED. However, no effective commercialized vaccine is available for controlling PED worldwide. A valid, safe, and cost-effective vaccine for controlling PEDVs is still urgently needed.

SUMMARY

One of the objectives of the present disclosure is to provide a useful tool to detect and/or prevent from porcine epidemic diarrhea virus infection. The useful tool could be a novel composition (which in some embodiments can also be known as a vaccine) and/or specific active ingredient thereof.

Another objective of the present invention is to provide a tool that could be useful in producing the aforesaid active ingredient.

In order to accomplish the aforesaid objectives, the present disclosure provides a baculovirus displaying porcine epidemic diarrhea virus spike (S) protein, S1 domain of the S protein, or porcine epidemic diarrhea virus nucleocapsid (N) protein.

The present disclosure also provides a pharmaceutical composition comprising the baculovirus of the present disclosure and a pharmaceutically acceptable carrier.

The present disclosure also provides an expression cassette comprising: a promoter; a first polynucleotide encoding SEQ ID NO: 04 (which is an envelope glycoprotein); and a second polynucleotide encoding porcine epidemic diarrhea virus spike (S) protein, S1 domain of the S protein or porcine epidemic diarrhea virus N protein.

The present disclosure also provides a cell comprising the expression cassette of the present disclosure.

The present disclosure further provides a method for evaluating porcine epidemic diarrhea virus infection, comprising: obtaining a sample from a subject to be evaluated; and contacting the sample with a baculovirus or a cell of the present disclosure.

BRIEF DESCRIPTION OF THE DRAWINGS

FIG. 1 shows the organization of the expression cassette and the construction maps of plasmids pTriEx-S, pTriEx-S1, and pTriEx-N of Experiment 1. The full-length S gene, polyneucleotide encoding S1 domain of S protein, and N gene are driven by the TriEx promoter, followed by the GP64 signal protein and 6×His-tag. The pTriEx-S contains the codon optimized full-length S gene. The pTriEx-S1 and pTriEx-N have the codon optimized S1 and N genes associated with GP64 transmembrane domain (TM-B) and the GP64 cytoplasmic domain (CTD-B) for membrane anchoring. All these constructs were also inserted with a mCherry fluorescent protein gene driven by the SV40-pag promoter as a reporter.

The mucosal PEDV spike-specific fecal IgA in piglets were detected at 0, 14, 28 days post-inoculation (DPI) by a PEDV specific in-house ELISA. Error bars indicated SD values corresponding to the six groups at each time point. Statistically significant differences were demonstrated as a and b ($p<0.05$). DPI: day post inoculation.

Figure 14:
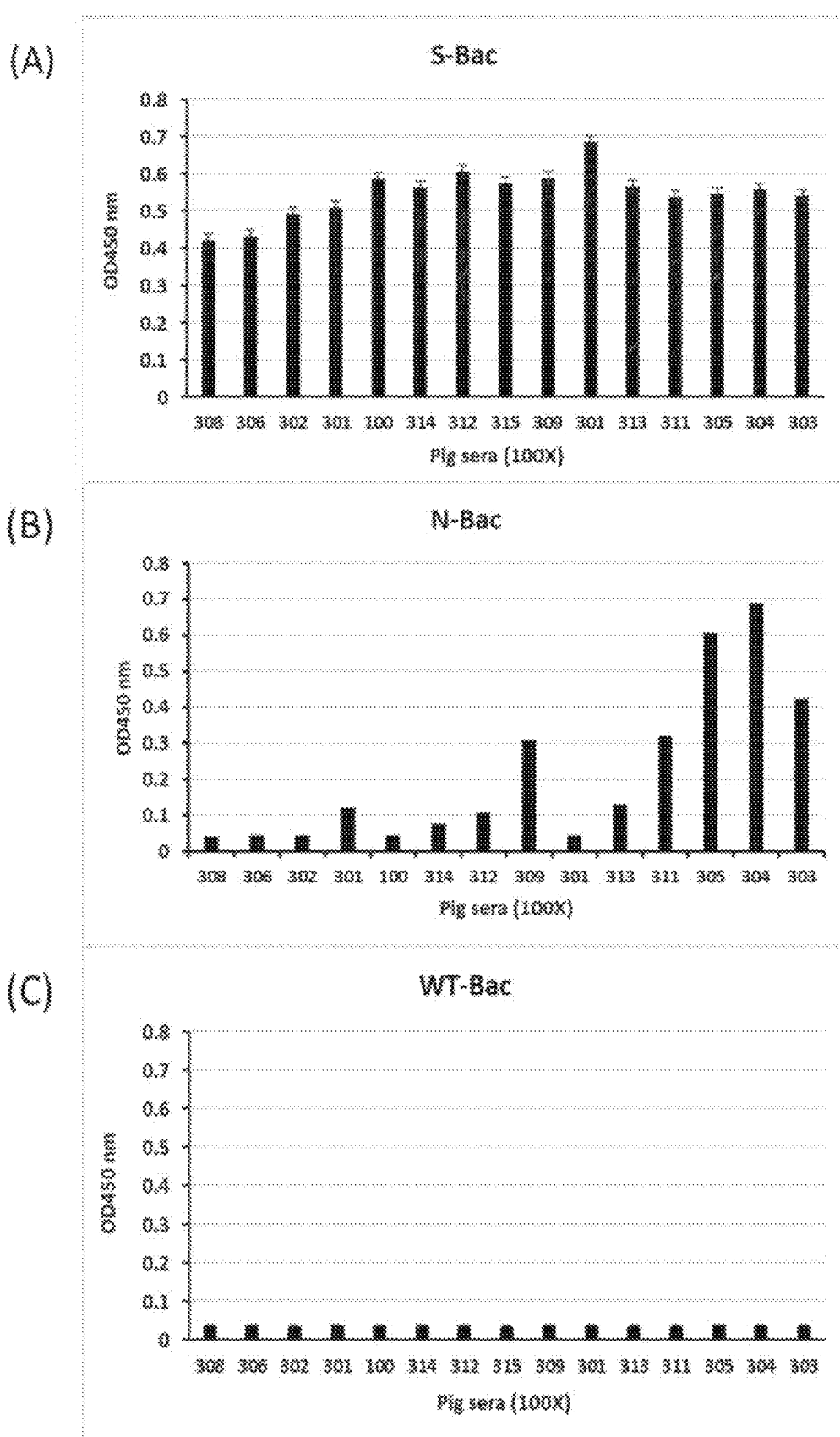

FIG. 14 shows the results of the insect cell-based ELISA for the detection of specific antibodies in piglets sera against PEDV. Sera were collected from both the specific pathogen free (SPF) piglets (lower panel) and after the infection of PEDV on these piglets (upper panel). Data express results obtained from infected and non-infected animals. Bars indicate the optical densities (OD) for each group.

DETAILED DESCRIPTION

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of"

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

It is to be understood that both the foregoing general description, including the drawings, and the following detailed description are exemplary and explanatory only and are not restrictive of this disclosure.

The technical and scientific terms used in the descriptions herein will have the meanings commonly understood by one of ordinary skill in the art, unless specifically defined otherwise.

As used herein, "preventing porcine epidemic diarrhea virus (PEDV) infection" or alike is referring to decreasing, moderating or obviating the level of infection of PEDV and/or the illness, syndrome, or disease caused by PEDV infection. Those having ordinary skill in the art can readily understand that in this field it is impossible to achieve zero infection. Thus, the aforesaid term has no intention to limit the present disclosure to achieve a result of no infection at all.

In the first aspect of the present invention, a baculovirus displaying porcine epidemic diarrhea virus S protein, S1 domain of the S protein, or porcine epidemic diarrhea virus N protein is provided. In a preferable embodiment, the porcine epidemic diarrhea virus S protein comprises SEQ ID NO: 01. In another preferable embodiment, the S1 domain of S protein comprises SEQ ID NO: 02. In yet another preferable embodiment, the N protein comprises SEQ ID NO: 3.

As used herein "comprises SEQ ID NO: XX" or alike means the protein/peptide (collected named protein hereinafter) may comprise other amino acids sequence other than the SEQ ID NO at issue as long as the protein maintains its function for the objectives of the present invention. For instance, those having ordinary skill in the art may construct a tag (such as His tag) with the SEQ ID NO at issue. The tag is just for purification purpose and would not affect the protein's function in view of the objectives of the present invention. In an alternative embodiment, the S protein is substantially consisted of SEQ ID NO: 01. In a specific embodiment, the S protein is consisted of SEQ ID NO: 01. In an alternative embodiment, the S1 domain of S protein is substantially consisted of SEQ ID NO: 02. In a specific embodiment, the S1 domain of S protein is consisted of SEQ ID NO: 02. In another specific embodiment, the N protein is substantially consisted of SEQ ID NO: 3. In yet another specific embodiment, the N protein is consisted of SEQ ID NO: 3.

It is particularly notable, in an embodiment that the baculovirus displays S1 domain of the porcine epidemic diarrhea virus S protein, the S1 domain exists isolated from the other parts of the S protein. That is to say, the S1 domain does not exist in its natural form. In its natural form, the S1 domain is part of the S protein and would not exist isolated because it is not an intact protein.

In a preferable embodiment, the baculovirus further displays an envelope glycoprotein; wherein the envelope glycoprotein comprises SEQ ID NO: 04. Without being bound by theory, the present disclosure suggests having the envelope glycoprotein is favorable for the baculovirus of the present disclosure to induce protective immune response in some circumstance. In a preferable embodiment, the envelope glycoprotein is GP64 signal peptide comprising GP64 transmembrane domain (TM-B) and GP64 cytoplasmic domain (CTD-B).

In a specific embodiment, the S protein and the envelope glycoprotein form a fusion protein comprising SEQ ID NO: 05. In another specific embodiment, the S1 domain and the envelope glycoprotein form a fusion protein comprising SEQ ID NO: 06. In yet another specific embodiment, the N protein and the envelope glycoprotein form a fusion protein comprising SEQ ID NO: 7. As used herein, "fusion protein" means, for instance, the polynucleotide encoding the envelope glycoprotein and the polynucleotide encoding the S1 domain are operably connected through a linkage or not so that the two polynucleotides are encoded together into a protein comprising a moiety of the envelope glycoprotein and a moiety of the S1 domain.

As used herein, "operably connected" means the two or more polynucleotides are connected in a way that the code can be correctly transcribed and translated. Specifically, a code to be translated into an amino acid constitutes three bases. Thus, the linkage between the two polynucleotides to be connected has to have three or three multiples bases; otherwise, the code of the later polynucleotide might be shifted into different code and encoded into wrong amino acid.

The second aspect of the present disclosure provides a pharmaceutical composition comprising the baculovirus of the present disclosure and a pharmaceutically acceptable carrier. Optionally, the pharmaceutical composition can further comprise an adjuvant.

As used herein, a "pharmaceutically acceptable" component (such as a carrier) means that the compound or composition is suitable for administration to a subject to achieve the treatments described herein, without unduly deleterious side effects in light of the severity of the disease and necessity of the treatment. "Carrier" means a material that does not cause significant stimulation to an organism and does not eliminate the biological activity and characteristics of a given compound. The carrier used in the present disclosure includes, but not limited to a buffer, excipient, stabilizer, preservatives, solvents, dispersion media, coatings, antibacterial and antifungal agents, isotonic and absorption delaying agents, and the like that are physiologically compatible.

As used herein, "adjuvant" has the same meaning as that well-known in medication/vaccine field. For example, said adjuvant is used for improving the immunogenic effect of said active ingredients, and/or stabilizing said active ingredients. The adjuvant used in the present disclosure includes, but not limited to, heat-labile enterotoxin B subunit (LTB), cholera toxin B (CTB), Chemokine (C-C motif) ligand 25, Chemokine (C-C motif) ligand 27, Chemokine (C-C motif) ligand 28, complete Freund's adjuvant, incomplete Freund's adjuvant, alumina gel, surfactant, anionic polymer, peptide, oily emulsion, or a combination thereof.

In an alternatively embodiment, the pharmaceutical composition can be formulated in a form of tablet, capsule, powder, suspension, or solution. In a specific embodiment, the pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The third aspect of the present invention provides an expression cassette comprising a promoter; a first polynucleotide encoding SEQ ID NO: 04; and a second polynucleotide encoding porcine epidemic diarrhea virus S protein or S1 domain of the S protein, or encoding porcine epidemic diarrhea virus N protein.

In a specific embodiment, the second polynucleotide encodes SEQ ID NO: 01. Alternatively, the second polynucleotide encodes SEQ ID NO: 02. Alternatively, the second polynucleotide encodes SEQ ID NO: 3. Practically, the first polynucleotide and the second polynucleotide might encode a fusion protein; wherein the fusion protein can be SEQ ID NO: 05, SEQ ID NO: 06, or SEQ ID NO: 7.

As used herein, "polynucleotide encodes" means the polynucleotide at issue can be converted into a polypeptide or protein through transcription and translation processes. The transcription and translation can be conducted in vitro or in vivo. When the transcription and translation is conducted in vivo (ex. in a cell of a particular organism), one shall be aware of the codon usage preference of the organism.

In a preferable embodiment, the expression cassette comprises SEQ ID NO: 11; the first polynucleotide encoding SEQ ID NO: 04; and the second polynucleotide encoding porcine epidemic diarrhea virus S protein, S1 domain of the S protein, or porcine epidemic diarrhea virus N protein. Preferably, the expression cassette can be constructed into a vector. In a specific embodiment, the vector is constructed based on pTriEx-3 plasmid (Novagen, Merck Biosciences, Darmstadt, Germany) having a TriEx promoter and 6×His tag. Alternatively, other promoters or other tags can be used. In an embodiment, the promoter can be operable for an insect cell or a mammalian cell. As used herein "operable" means the promoter can be recognized and used by the organism at issue for initiating the transcription and translation.

The fourth aspect of the present invention provides a cell comprising the expression cassette of the present disclosure. Alternatively, the cell could be an insect cell including but not limited to Sf21, Sf9, Hi5, or BmN cells.

The fifth aspect of the present invention provides a method for evaluating porcine epidemic diarrhea virus infection, comprising: obtaining a sample from a subject to be evaluated; and contacting the sample with a baculovirus or a cell of the present disclosure In a preferable embodiment, the sample is a serum. The term "contacting" can be achieved by mixing the sample with a suspension/solution of the baculovirus or the cell. In an alternative embodiment, the baculovirus or the cell is coated on a surface and then the sample is introduced to achieve the "contacting" step.

In a preferable embodiment, the method further comprises a step after the contacting step; wherein the step is to detect the interaction between the sample and the baculovirus or the sample and the cell. The term "interaction" can be construed as, for instance, the binding between the sample and the baculovirus/cell. In a specific embodiment, the method can be conducted by using an ELISA assay and the detecting can be achieved by a spectrophotometer.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Materials and Methods 1.1 Viruses and Cell Lines

The high virulent PEDV Pintung 52 passage 5 (PEDV-PT-P5) (GenBank Accession No. KY929405) viral stock was used for preparation of the PEDV-PT passage 6 (PEDV-PT-P6) and PEDV-PT passage 7 (PEDV-PT-P7) in Vero cells (American Type Culture Collection (ATCC) No. CRL-1586) as previously described (Chang, Y. C. et al, Viruses 2017, 9, (5)). A viral challenge stock of PEDV-PT-P6&7 was prepared by admixing 1:1 ratio of the PEDV-PT-P6 and PEDV-PT-P7 supernatants. The titer of the PEDV-PT-P6&7 viral stock was determined as $10^5$ TCID50/mL by performing a 10-fold serial diluted inoculation on Vero cells.

1.2 Plasmid Construction

Figure 1:
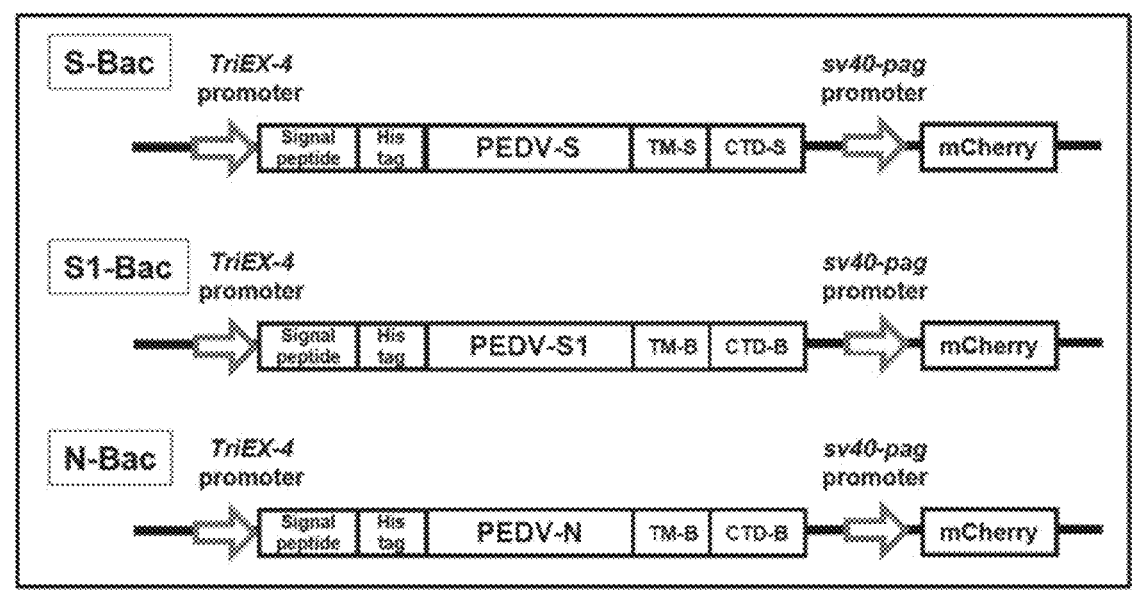

The nucleotide sequence of S gene derived from the Taiwan G2b PEDV-PT strain (Genbank accession No. KP276252) and N gene (GenBank accession No. AEZ68021.1) was codon optimized for insect cells and synthesized by ProTech (ProTech, LA, USA). The PEDV full length S gene, polynucleotide encoding S1 domain of S protein, and N genes were cloned into pTriEx-3 plasmid (Novagen, Merck Biosciences, Darmstadt, Germany), bringing pTriEx-S, pTriEx-S1 and pTriEx-N, respectively (See FIG. 1) (having the expression cassette for these proteins or domain of the present invention comprising SEQ ID NO: 11). The pTriEx-3 plasmid contains tripartite p10, CMV and T7 promoters for the convenient expression in insect, mammalian, and bacterial cells. The full-length S, S1 and N protein sequences were driven by TriEx promoter with 6×His-tag in plasmids pTriEx-S, pTriEx-S1 and pTriEx-N, respectively (FIG. 1). The mCherry gene was driven by the binary sv40-pag promoter for emitting reporter fluorescence in Sf21 and mammalian cells. The plasmids were constructed according to the instructions' manual of In-Fusion® HD Cloning Kit (Clontech Laboratories Inc, CA, USA).

1.3 Recombinant Baculovirus Preparation

Plasmids pTriEx-S, pTriEx-S1 and pTriEx-N were co-transfected with FlashBAC™ (Mirus, WI, USA) DNA into Sf21 cells by Cellfectin (Life Technologies, CA, USA) to further generate recombinant baculoviruses, S-Bac, S1-Bac and N-Bac. The expression of mCherry gene product and 6×His-tag are used to trace proper viral infection and protein expression. The S-Bac, S1-Bac and N-Bac virus clones with high titers were selected and used for subsequently recombinant baculoviruses production.

1.4 Western Blotting

The infected cell lysates were subjected to gradient sodium dodecyl sulfate (SDS)-polyacrylamide electrophoresis (PAGE) gel (HR gradient gel solution, TOOLS, Taiwan). After electrophoresis, proteins were transferred to PVDF membranes. The protein signals were detected by using mouse anti-6×His-tag monoclonal antibody (1:5000 dilution, EnoGene, NY, USA). Then, the goat anti-mouse IgG conjugated to HRP (1:5000 dilution, Invitrogen, CA, USA) were used as the secondary antibodies for signal detection. The protein bands were detected by using the Clarity™ Western ECL Blotting Substrates (Bio-Rad) using Classic Blue Autoradiography film BX (Life Science, MO, USA).

1.5 Characterizations of S-Bac and S1-Bac by Electron Microscopy (EM)

Supernatants were collected from the S-Bac-inoculated and S1-Bac-inoculated Sf21 cells. The cell debris was coarsely removed by centrifugation at 10,000 rpm for 30 min, then the supernatants were collected and subjected onto the 25% (w/w) sucrose cushion in SW28 tubes (Beckman, CA, USA) for centrifugation at 24,000 rpm for 80 min in 4° C. to obtain the viral pellet. After discarding the supernatant, the viral pellets were resuspended with 1 mL PBS, then subjected to a 25-60% (w/w) sucrose gradient at 28000 rpm for 3 hours (hrs). Viral particles were collected and washed with PBS to remove sucrose. These purified viral particles were then fixed, labeled with anti-His immunogold, and visualized by electron microscopy (EM) with negative staining as described in previous studies. Briefly, an aliquot of 10 µL virus particles preparation was loaded onto a carbon-coated grid, letting standstill for 5 min. Grids were then stained with 2% of phosphotungstic acid (PTA) for 1 min, then, the excess PTA was drained and completely dry-out, the grids were examined directly under EM. For immunogold labeling, virus particles were loaded onto a collodion-coated EM grid for 5 min. After the removal of excess viral particles by gently blotting with a filter paper at the edge of the grid, an anti-His tag antibody (Invitrogen) was added onto the grid and incubated for 1 hr at room temperature. Grids then underwent 10 s wash for six times in PBS at room temperature and were incubated with 6 nm gold-conjugated anti-mouse IgG for 1 hr. After six times of washes in PBS, the grids were stained with 2% PTA for 1 min, then drained and dry-out, then examined under the EM.

1.6 Immunization Program of Mice

Twelve Balb/c mice were randomly divided into three groups: control, S-Bac, and S1-Bac groups. The mice were immunized intramuscularly on the thigh with either S-Bac or S1-Bac, by a dosage of 200 µL of $10^9$ TCID50/mL per shot. The mice in the control group were injected with 200 µL of the cell culture medium of Sf21. The injections were given two times with 2-week intervals. The blood was collected at day 0 (pre-priming), 14 (2 weeks after priming), and 28 (2 weeks post-boosting) for evaluating the change of PEDV-specific IgG.

1.7 Immunization Program of Piglets

Fifteen five-week old, Large White x Duroc, crossbred, PEDV-seronegative, and fecal PEDV shedding negative pigs were screened for our experimental applications. All piglets were labeled by ear tags, stochastically separated into three groups, including the control group, the S1-Bac IM injection group, and the S-Bac IM injection group, and housed in three separate rooms. Each group of pigs were intramuscularly injected with 2 mL control medium, 2 mL of $10^9$ TCID50/mL S1-Bac, or 2 mL of $10^9$ TCID50/mL S-Bac on both sides of thigh two times at a two-weeks interval. At day 28, all pigs were orally challenged with 5 mL of $10^5$ TCID50/mL PEDV-PT-P6&7. After challenging, the clinical signs were scored and the rectal swabs were collected every day to monitor the viral shedding and mucosal IgA. The blood was collected every two weeks in order to evaluate the PEDV S protein-specific plasma IgG. All animal experiment procedures performed on the animal were reviewed and approved by the Institutional Animal Care and Use Committee of National Taiwan University (Taipei, Taiwan, NTU106EL-00054).

1.8 Clinical Scoring

The clinical signs of each pig were observed and recorded every day. The condition of diarrhea that associated with PEDV challenging was scored into four levels: 0, normal stool; 1, loose consistency of the stool; 2, semi-fluid consistency of the stool; 3, watery diarrhea. Additionally, pigs of each group were weighted every two weeks.

1.9 ELISA for Detecting Systemic IgG

The purified recombinant S protein displayed by HEK 293 cells as previously described was coated on the ninety-six well, Nunc maxi-soap plate (Thermo Fisher Scientific, Massachusetts, USA) with the concentration of 2 µg/µL diluted in coating buffer (KPL, SeraCare, MA, USA) at 4° C. for 16 hrs. The S coated plates were firstly washed six times with 200 µL washing buffer (KPL, SeraCare) and blocked with blocking buffer (KPL, SeraCare) at room temperature (RT) for 1 hr. After centrifuging at 3000 rpm for 30 minutes and removing the blood cells, the blood samples of mice and pigs were diluted 40-fold in blocking buffer (KPL, SeraCare) and followed by 1 hr incubation on the S coated plates at RT. The plates were washed six times in 200 washing buffer (KPL, SeraCare) after incubation, and the antibodies were detected by either using 1000× diluted horseradish peroxidase (HRP) conjugated goat anti-mouse IgG (KPL, SeraCare) or HRP conjugated goat anti-pig IgG (KPL, SeraCare) in blocking buffer (KPL, SeraCare). After 1 hr incubation, the plates were washed six times with 200 µL washing buffer (KPL, SeraCare). Fifty microliter of ABTS® Peroxidase Substrate System (KPL, SeraCare) was added each well at RT for 10 minutes. The reaction was stopped by adding 50 µL stopping solution (KPL, SeraCare), and the optical density (OD) was read at a wavelength of 405 nm by EMax Plus Microplate Reader (Molecular Devices, Crawley, UK). The result was expressed as sample to positive ratio (S/P ratio).

1.10 ELISA for Detecting Mucosal IgA

Each rectal swab was resuspended in 1 mL PBS and was two-fold diluted in blocking buffer (KPL, SeraCare). The ELISA procedures were as mentioned above, with the modifications of incubating the suspension supernatants for 16-18 hrs under 4° C. and followed by a 1 hr incubation of secondary antibody of goat anti-pig IgA (KPL, SeraCare) to detect the fecal IgA with 20 min of coloration time.

1.11 RNA Extraction, cDNA Synthesis, and Probed Quantitative Real-Time PCR

Each rectal swab was resuspended in 1 mL PBS, and 200 µL of each supernatant was used for RNA extraction. The procedures of RNA extraction were performed by QIAcube HT (Qiagen, Chatsworth, Calif., USA) using a QIAamp cador Pathogen Mini Kit (Qiagen), according to the manufacturer's instructions. Complementary DNA (cDNA) synthesis was performed by reverse transcription using the QuantiNova Probe PCR Kit (Qiagen). The real-time PCR was modified according to a previously established method using the specific probe (3'-FAM-TGYYACCAYYAC-CACGACTCCTGC-BHQ1-5'; SEQ ID NO: 12), PEDV-N forward primer (3'-CGCAAAGACTGAACCCACTAAC-5'; SEQ ID NO: 13), and PEDV-N reverse primer (3'-TTGCCTCTGTTGTTACTTGGAGAT-5'; SEQ ID NO: 14). The real-time PCR condition was 95° C. for 2 min and 45 cycles of 95° C. for 15 s and 55° C. for 15 s.

1.12 Neutralizing Assay

The plasma samples of each pig were incubated at 56° C. for 30 min to inactivate the complement. The procedure of neutralizing assay was performed as previous published with some modifications. Briefly, the plasma samples were diluted from 10-fold to 320-fold in Dulbecco's modified Eagle's medium (DMEM) (Gibco, Gaithersburg, USA). Fifty microliter of the diluted plasma samples was mixed with an equal volume of 200 TCID50/mL of PEDV-PT-P6&7. After incubating at 37° C. for 1 hr, the mixture was added onto the Vero cells grown on 96 well plates with a 90% confluence. The cells were incubated at 37° C. for 1 hr and followed by two washes of DMEM and replaced by 100 μL of the fresh post-inoculation (PI) medium, which contained DMEM (Gibco, Gaithersburg, USA) supplemented with tryptose phosphate broth (0.3%) (Sigma, Missouri, USA), yeast extract (0.02%) (Acumedia, CA, USA), and 10 μg/mL of trypsin (Gibco, Gaithersburg, USA). The cytopathic effect (CPE) was observed at 24 hrs. The neutralizing titers of each plasma were calculated as the reciprocal of the highest dilutions without CPE.

1.13 Statistical Analysis

The results of IgG level, IgA level, body weight, antibody titer, and viral shedding were compiled statistics with SAS 9.4 (Statistical Analysis System, SAS Institute Inc., Cary, N.C., USA). The differences between each group were compared by one-way analysis of variance (ANOVA). The significance was determined to have a p-value <0.05 ($p<0.05$).

1.14 S-Bac, S1-Bac, and N-Bac Infected Cell-Based ELISA

The S-Bac, S1-Bac, and N-Bac infected SF21 cells were separately coated on the ninety-six well, Nunc maxi-soap plate (Thermo Fisher Scientific, Massachusetts, USA) with $4 \times 10^4$ cells at 26° C. for 1 hrs. These recombinant baculovirus-infected SF21 cell coated plates were firstly fixed with 4% paraformaldehyde for 15 minutes, then washed three times with 200 μL PBST and blocked with blocking buffer at room temperature for 1 hr. After centrifuging at 3000 rpm for 30 minutes and removing the blood cells, the blood samples of pigs were diluted 100-fold in blocking buffer and followed by 1-hour incubation on the recombinant baculovirus-infected cell coated plates at RT. The plates were washed three times in 200 μL PBST after incubation, and the antibodies were detected by using 1000× diluted HRP conjugated goat anti-pig IgG in blocking buffer. After 1 hr incubation, the plates were washed six times with 200 μL PBST. 50 μL 1-Step Ultra TMB-ELISA reagent was added each well at RT for 20 minutes. The reaction was stopped by adding 50 μL stopping solution, and the optical density (OD) was read at a wavelength of 450 nm by EnSpire Series Multilabel Plate Readers.

Figure 2:
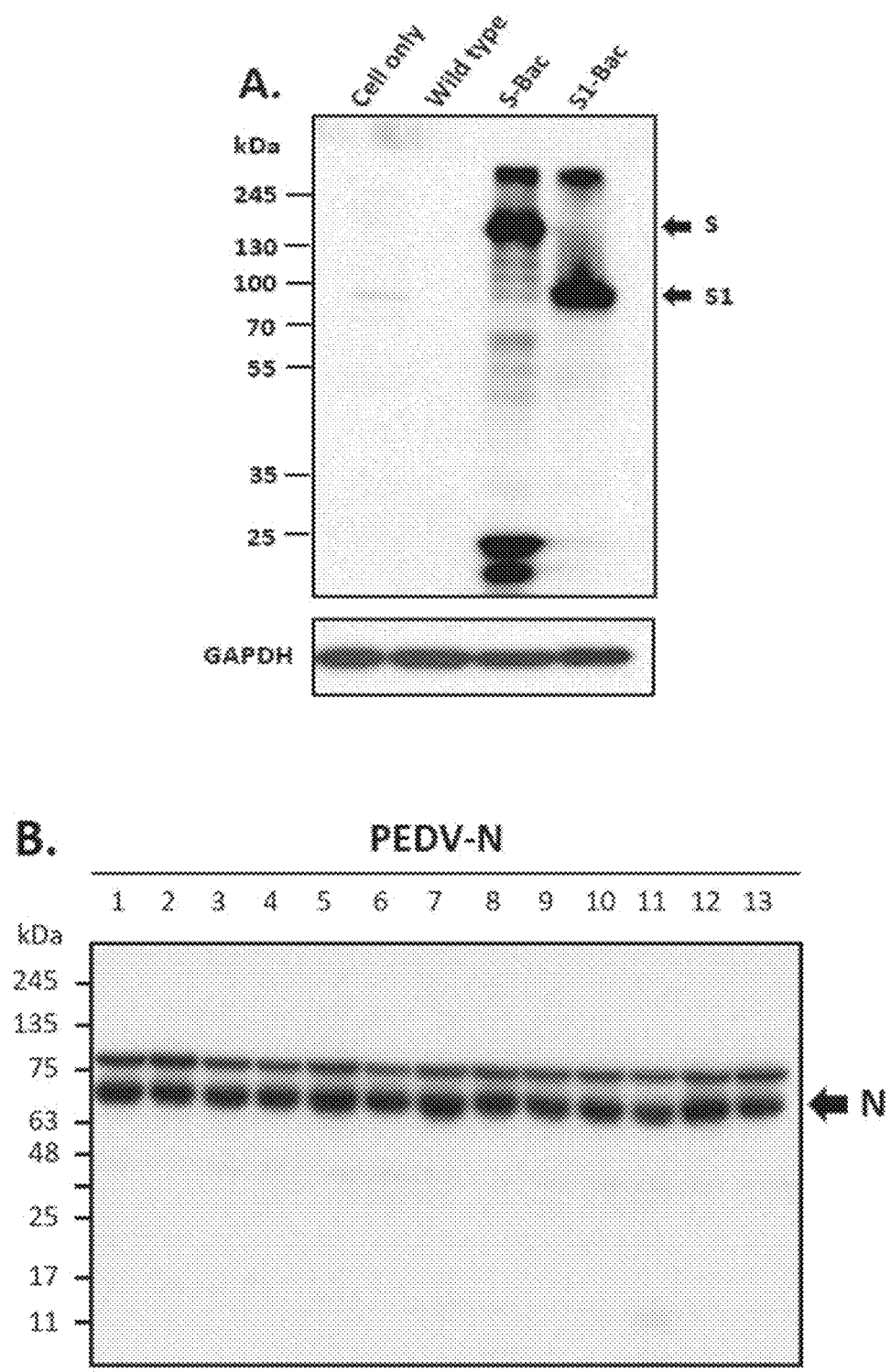
FIG. 2 shows the result of Western blotting analysis in Experiment 1. The detection of porcine epidemic diarrhea virus (PEDV) full-length S proteins, S1 domain of S protein, and N proteins in the cell lysate of S-Bac, S1-Bac and N-Bac infected Sf21 cells at 3 days post infection with an M.O.I. of 5. Western blotting analysis of PEDV S, S1 and N proteins displaying by baculoviruses was performed and probed with anti-His tag antibodies. The corresponding molecular weights of S, S1 and N proteins were approximately 200 kDa, 100 kDa and 70 kDa, respectively. Cell only: the non-infected Sf21 cell; Wild-type: Sf21 cells infected with wild type AcMNPV; S-Bac: Sf21 cells infected with S-Bac; S1-Bac: Sf21 cells infected with S1-Bac; GAPDH: control cellular protein for equal volume loading.

Experiment 1: Display of PEDV Full Length S Protein, S1 Domain and N Protein by Recombinant Baculoviruses, S-Bac, S1-Bac and N-Bac After propagating S-Bac, S1-Bac, and N-Bac derived from co-transfection of pTriEx-S, pTriEx-S1, and pTriEx-N separately with AcMNPV baculovirus genome in the Sf21 cells, the Sf21 cells were lysed and analyzed by western blotting for evaluating the display of S protein, S1 domain, and N proteins. The positive signals of the S protein, S1 domain, and N proteins were observed at the sizes 200 kDa, 100 kDa, and 70 kDa, respectively (FIG. 2). As a negative control, no detectable signal was observed in the lysate of Sf21 cells infected with wild-type AcMNPV virus.

Experiment 2: The Visualization of S Protein and S1 Domain Displayed on the Surface of S-Bac and S1-Bac by Electron Microscopy (EM)

Figure 3:
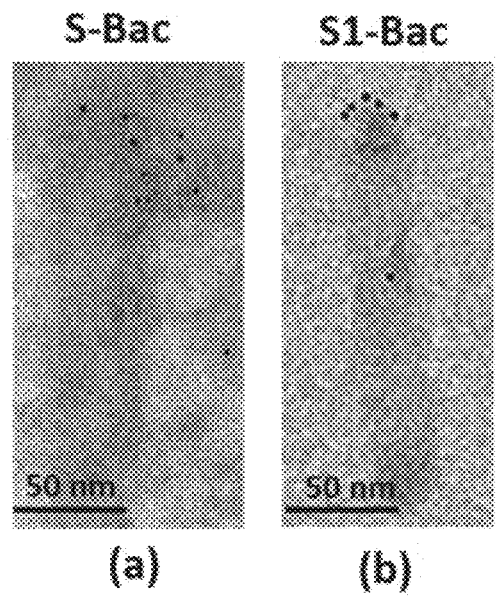
FIG. 3 shows the electron microscopy detection in Experiment 2. The electron micrographs demonstrated positive colloid gold signals of porcine epidemic diarrhea virus (PEDV) full-length S and S1 proteins on the surface of recombinant S-Bac (a) and S1-Bac (b), respectively. The bars represent a reference for 50 nm.

To investigate whether the S protein or S1 domain were displayed on the recombinant baculoviruses, the viral particles of S-Bac and S1-Bac collected and purified from culture supernatants were probed with colloid gold-labeled antibodies and examined by EM. As shown in FIG. 3, the EM images revealed regular long-rod shaped virions in approximate sizes of 200 nm with clear colloid gold particles on the apex of both S-Bac (FIG. 3a) and S1-Bac (FIG. 3b) virions. Suggesting both full length S and S1 could be properly anchored on the envelope of baculovirus.

Experiment 3: Systemic PEDV S-Specific IgG in Mice

Figure 4:
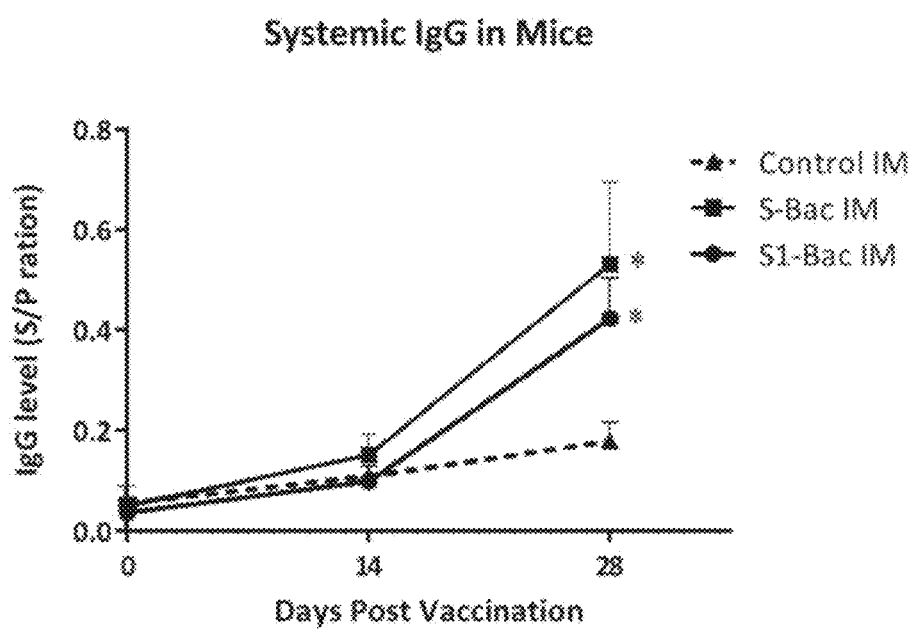
FIG. 4 shows the changes of systemic porcine epidemic diarrhea virus (PEDV) spike-specific IgG levels in S-Bac and S1-Bac vaccinated mice. The serum samples of the mice were collected three times in two-week intervals, including day 0 (pre-priming), 14 (2 weeks post-priming), and 28 (2 weeks post-boosting). The systemic anti-PEDV S protein IgG levels were detected by the PEDV S protein-based ELISA. The X axis represented the day post vaccination; whereas the Y axis showed the sample-to-positive control ratios (S/P ratio) of the optical density (OD) values from ELISA. The S/P ratio was defined as the ratio of the difference between the OD values of sample and negative control and the difference between OD values of positive and negative controls. The error bars represented the SD values of each group in different time points. The solid line with square icon and the gray line with round icon represent the climbing trend of IgG level in the S-Bac group and S1-Bac group, respectively. The IgG levels in the control group was expressed as the dotted line with triangle icon. *: significant difference with the control group (p<0.05).

To evaluate the immunogenicity of S1-Bac and S-Bac, the PEDV S specific blood IgG levels were determined at day 0 (pre-priming), 14 (2 weeks post-priming), and 28 (2 weeks post-boosting) in mice using a PEDV S-based indirect ELISA. The mean sample-to-positive control ratios (S/P ratio) was analyzed and shown in FIG. 4. At day 14 (2 weeks post-priming), the mean S/P ratio of systemic IgG levels in mice were 0.15±0.04 and 0.1±0.03 in S-Bac and S1-Bac groups, respectively, and had no significant difference from that of the control group. At day 28 (2 weeks post-boosting), the mean S/P ratio of PEDV S specific IgG levels were elevated to 0.53±0.16 and 0.42±0.08 in S-Bac and S1-Bac groups, respectively, and were significantly higher than those of the control group, 0.18±0.04. No statistical difference of the systemic PEDV specific IgG levels was observed between the S1-Bac and S-Bac groups during the study.

Experiment 4: Neutralizing Antibody Titer in Blood of Mice

Figure 5:
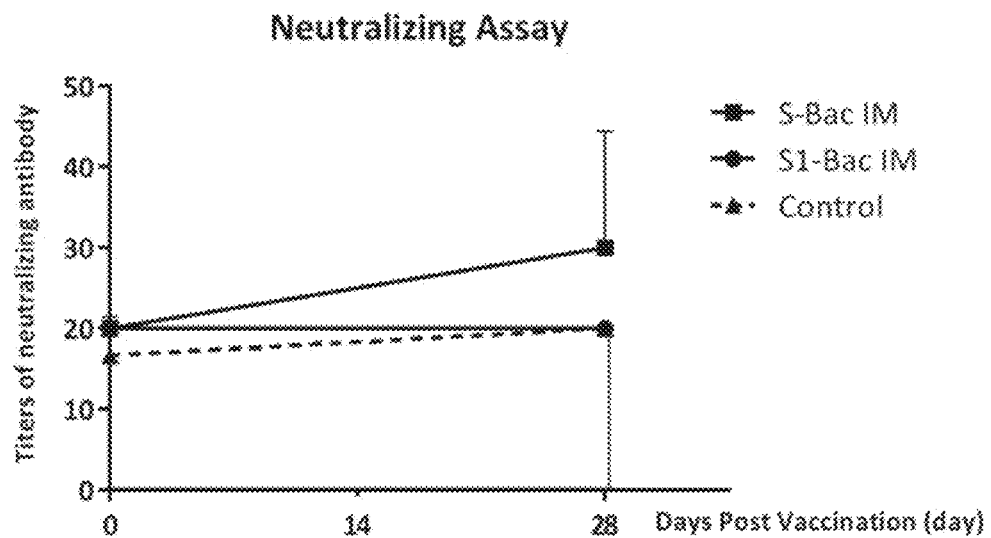
FIG. 5 shows the neutralizing titers of systemic antibody of mice in control, S-Bac and S1-Bac groups at day 0 (pre-priming) and day 28 (2 weeks post-boosting). The shift of neutralizing titers of S-Bac and S1-Bac vaccinated mice were represented as solid line with square icons and gray line with round icons, respectively. The neutralizing titers in blood of control mice were labeled with triangle icons on a dotted line. The error bars represented the SD values of each group in different time points. *: significant difference with the control group ($p<0.05$). The background of this neutralizing assay was 1:20, and the area under detection background was marked with gray zone.

The neutralizing antibodies against PEDV-PT in serum of mice were analyzed. As shown in FIG. 5, there was no detectable neutralizing antibody in all groups at day 0 (pre-priming). At 2 weeks post-boosting, the average neutralizing antibody titer in the S-Bac group was elevated and reached to 1: 30±14.

Figure 6:
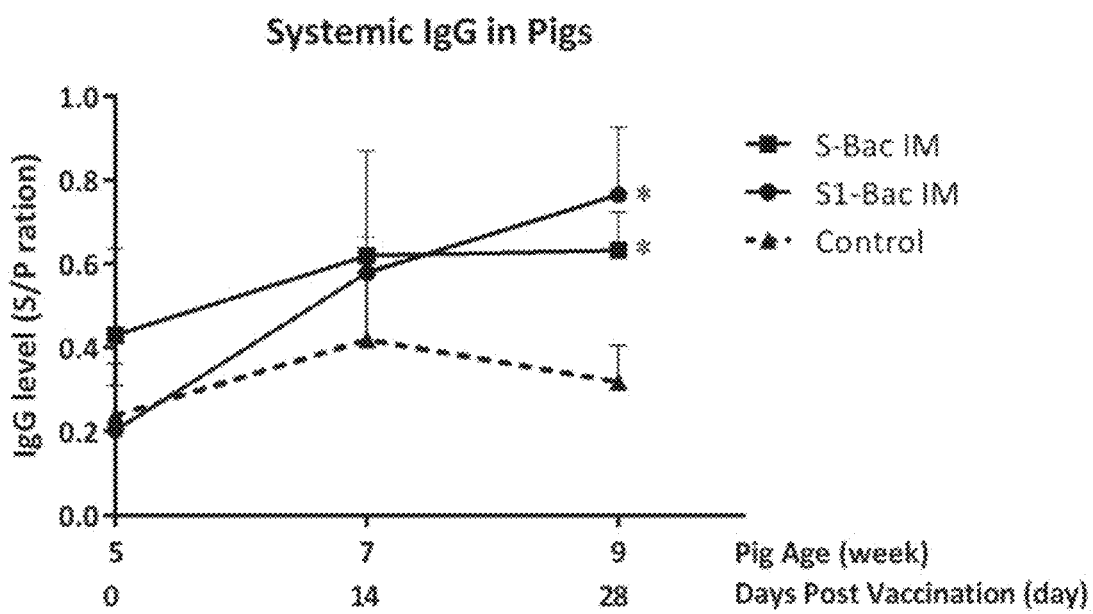
FIG. 6 shows the systemic anti-porcine epidemic diarrhea (PEDV) spike-specific IgG levels in piglets after S-Bac or S1-Bac vaccination. The systemic IgG levels of piglets were detected every two weeks at day 0 (pre-priming), day 14 (2 weeks post-priming) and day 28 (2 weeks post-boosting) by using the PEDV S-based ELISA. The data was shown as the mean values of the sample-to-positive control ratios (S/P ratio) which was defined as the difference between the optical density (OD) values of sample and negative control and divided by the difference between OD values of the positive and negative control. The error bars represented the SD values of each group in different time points. The solid line with square icon and the gray line with round icon represent the climbing trend of IgG level in the S-Bac group and S1-Bac group, respectively. The IgG level in the control group was expressed with the dotted line with triangle icon. *: significant difference with the control group ($p<0.05$).
Figure 7:
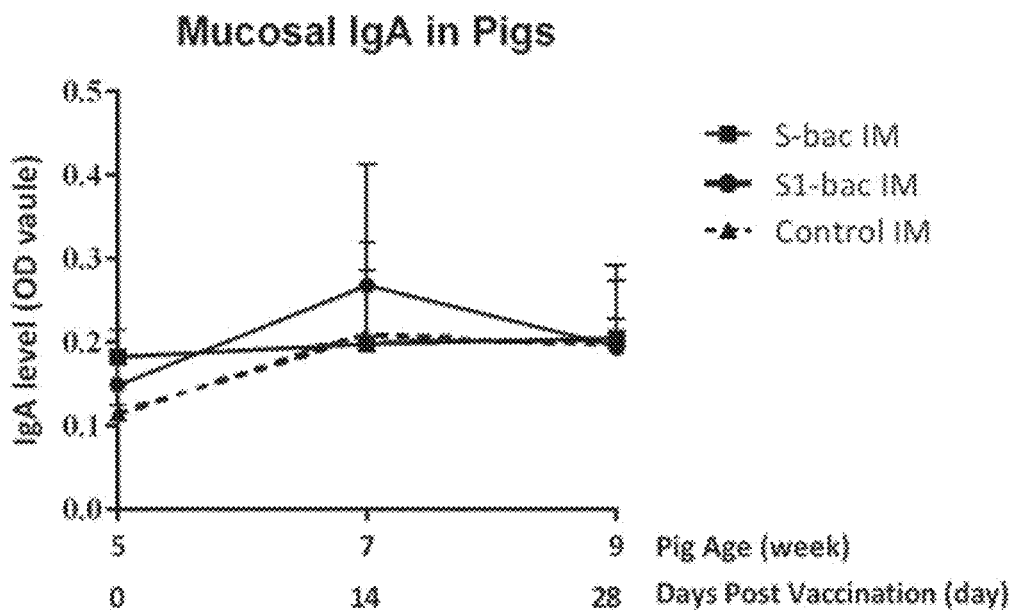
FIG. 7 shows the anti-porcine epidemic diarrhea (PEDV) spike-specific fecal IgA levels in piglets after S-Bac or S1-Bac immunizations. The mucosal IgA levels of pigs were evaluated every two weeks at day 0 (pre-priming), day 14 (2 weeks post-priming) and day 28 (2 weeks post-boosting) from rectal swabs by using PEDV—S based ELISA. The data was present as mean OD values from five pigs. The error bars represented the SD values of each group in different time points. The solid line with square icon and the gray line with round icon represent the climbing trend of IgA level in the S-Bac group and S1-Bac group, respectively. The IgA levels in the control group was expressed with the dotted line with triangle icon. *: significant difference with the control group ($p<0.05$).

Experiment 5: Systemic PEDV S-Specific IgG and Fecal PEDV S-Specific IgA in Pigs To estimate the systemic immune responses against PEDVs, the plasma IgG was evaluated at day 0 (pre-priming), 14 (2 weeks post-priming), and 28 (2 weeks post-boosting). The mean S/P ratio was analyzed and shown in FIG. 6. At day 14 (2 weeks post-priming), the mean S/P ratio of systemic IgG levels of pigs in S-Bac and S1-Bac group rise to 0.62±0.25 and 0.58±0.08, respectively. At day 28 (2 weeks post-boosting), the mean S/P ratio of IgG levels of pigs were significantly elevated to 0.63±0.09 and 0.77±0.16 in both S-Bac and S1-Bac group, respectively, with significant differences ($p<0.05$) from that of the control group. As to the PEDV-S specific mucosal IgA level (FIG. 7), the IgA level was slightly elevated in the S1-Bac group at day 14 (2 weeks post-priming).

Experiment 6: Neutralizing Antibody Titer in Blood of Pigs

Figure 8:
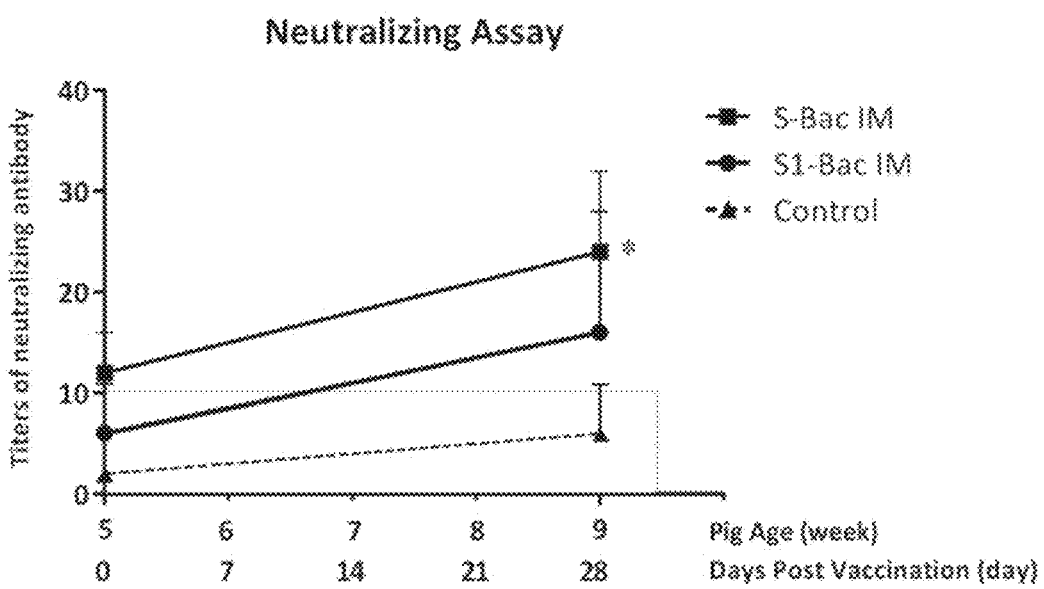
FIG. 8 shows the neutralizing titers against porcine epidemic diarrhea virus (PEDV) in each group at day 0 (pre-priming) and day 28 (2 weeks post-boosting). A solid line with square icons, a gray line with round icons, and a dotted line with triangle icons represent the titers of anti-PEDV neutralizing antibodies of pigs in the S-Bac, S1-Bac, and control group, respectively. Values were present in means±SD. The gray zone resembled the background of neutralizing assay. *: significant difference with the control group ($p<0.05$).

The mean titers of neutralizing antibody against PEDV-PT strain in different groups were present in FIG. 8. During the study, different levels of neutralizing antibody against PEDV-PT strain were detected in both S1-Bac and S-Bac immunized groups. No neutralizing antibody against PEDV-PT strain was detected in the control group. At day 28 (2 weeks post-boosting), the neutralizing titers of the S1-Bac and S-Bac groups were 1:16±12 and 1:24±8, respectively.

Experiment 7: Body Weights of the Pigs

Figure 9:
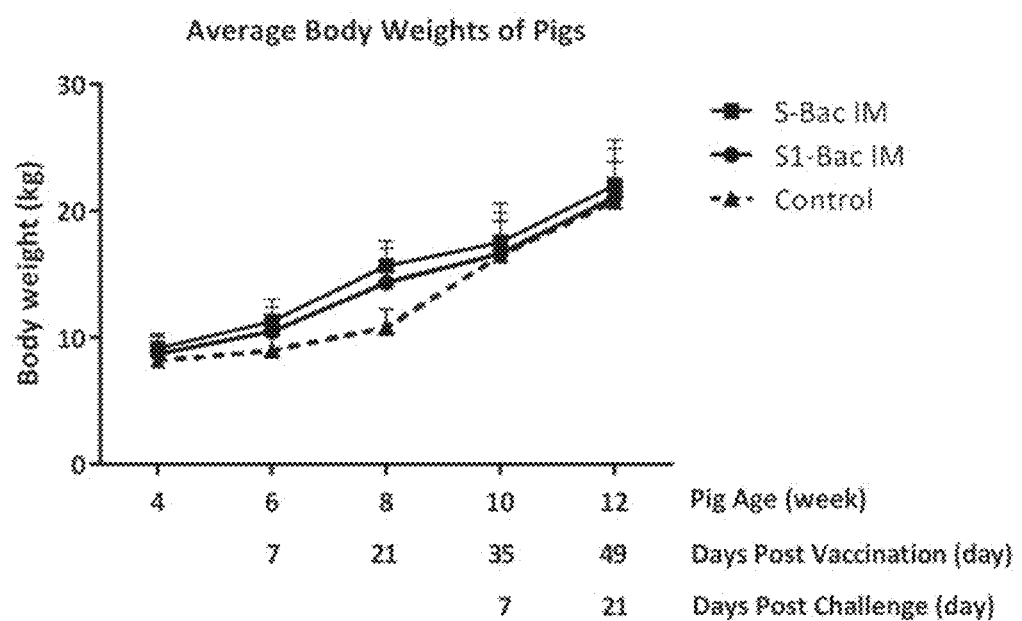
FIG. 9 shows the average body weight of piglets in each group in the experiments of the research of the present disclosure. The body weight of the piglets was measured in a two-week interval since the piglets were 4-week-old. The X axis was the time line indicating the age of the piglets, day post vaccination, and day post challenge. The piglets were vaccinated twice at 5-week-old and 7-week-old (labeled with white arrow); the piglets were challenged with $5\times10^5$ TCID50 PEDVPT-P6&7 at 9-week-old (labeled with black solid arrow). The Y axis was the averaged body weights of five piglets in each group. The error bars represented the SD values of each group in different time points. The solid line with square icon and the gray line with round icon represent the average body weight of pigs in the S-Bac group and S1-Bac group, respectively. The average body weight of pigs in the control group was expressed as the dotted line with triangle icon. *: significant difference with the control group ($p<0.05$).

During the study, the body weight of each piglet was monitored every two weeks after being introduced into the animal facility (FIG. 9). Although pigs in the control group showed slightly less weight gain during the vaccination period as compared with S1-Bac and S-Bac groups, no significant difference of body weight was observed among all groups during the study. Suggesting that the vaccines have no obvious adverse effect to the piglets.

Experiment 8: Clinical Scoring

Figure 10:
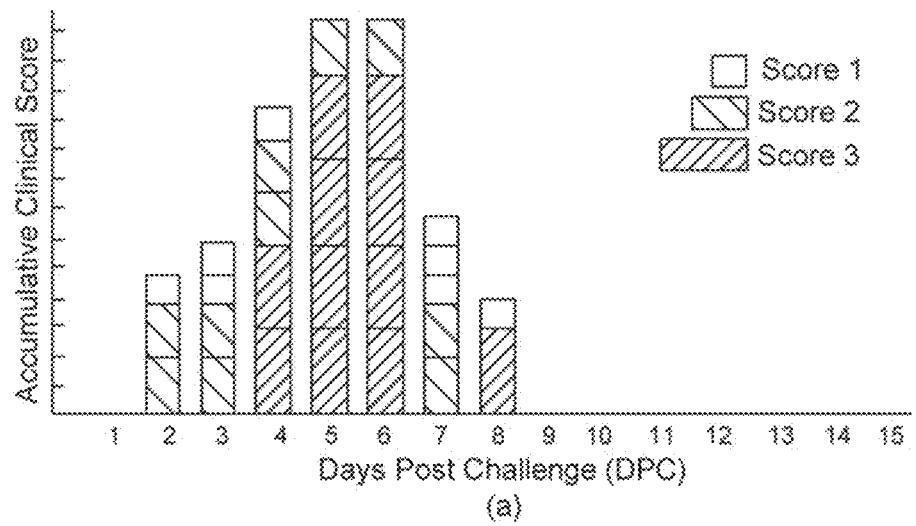
FIG. 10 shows the accumulations of clinical scores in the control group (a), S1-Bac group (b), and S-Bac (c) groups after the high virulent porcine epidemic diarrhea virus (PEDV-PT) challenge. The clinical signs were scored by the following rules: 0, normal stool; 1, loose consistency of the stool; 2, semi-fluid consistency of the stool; 3, watery diarrhea. Each piglet was orally challenged with $5\times10^5$ TCID50 PEDV-PT-P6&7 at day post vaccination 28 (day post challenge 0). A total of 15 days observation period was taken after challenge. The blank square resembled the score 1 (loose consistent stool); the light-grey square represented the score 2 (semi-fluid stool); the dark-grey square resembled the score 3 (watery diarrhea).
Figure 10:
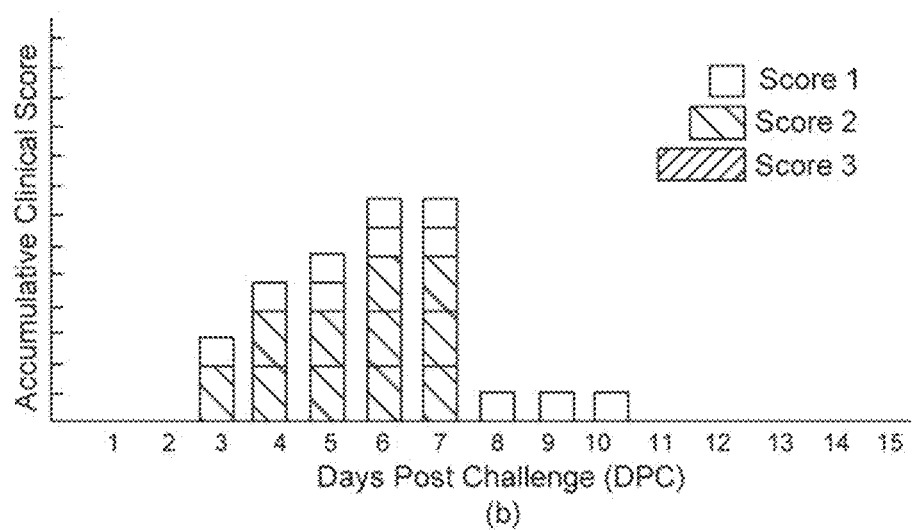
Figure 10:
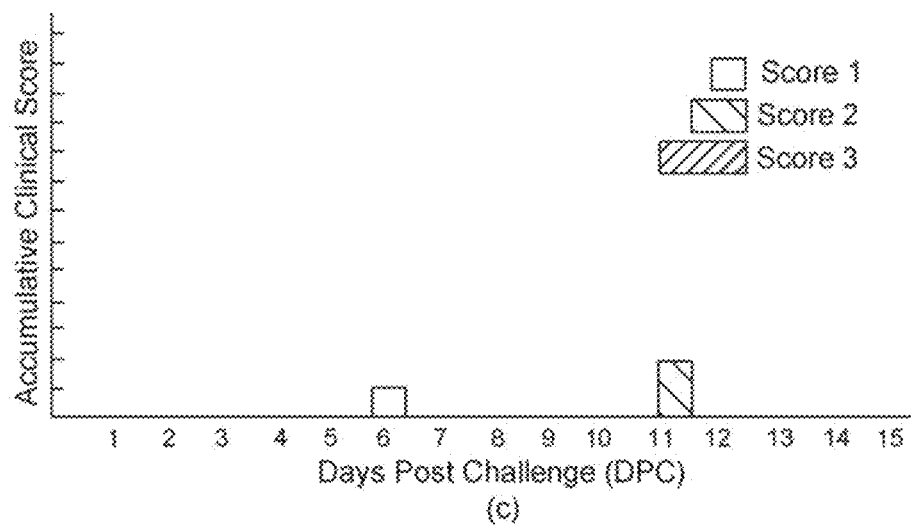

Before the PEDV-PT challenge, no clinical signs were observed in all groups. After orally challenging pigs with PEDV-PT-P6&7 (FIG. 10), three of five pigs (3/5) in the control group present mild to moderate diarrhea, which were scored as 1 to 2, at 2 days post challenge (DPC). At 4-7 DPC, all pigs in the control group showed moderate to severe clinical signs. During the study, all pigs in the control group had 5-6 days of watery diarrhea (score 3) and recovered at 9 DPC. Comparatively, the S-Bac and S1-Bac immunized pigs showed a decrease of the overall severity of diarrhea, delay onset of the disease and shorten the course of the illness as compared with pigs in the control group. In the S1-Bac immunized group, the appearance of clinical signs was postponed to 3 to 4 DPC and all pigs showed milder symptoms, which were scored 1 to 2, as compared with the control group during the study. In the S-Bac immunized group, importantly, four of five (4/5) pigs presented no clinical symptoms during the study, excepting one pig had soft feces (score 1) at 6 DPC and semifluid feces (score 2) at 11 DPC.

Experiment 9: Fecal Viral Shedding

Figure 11:
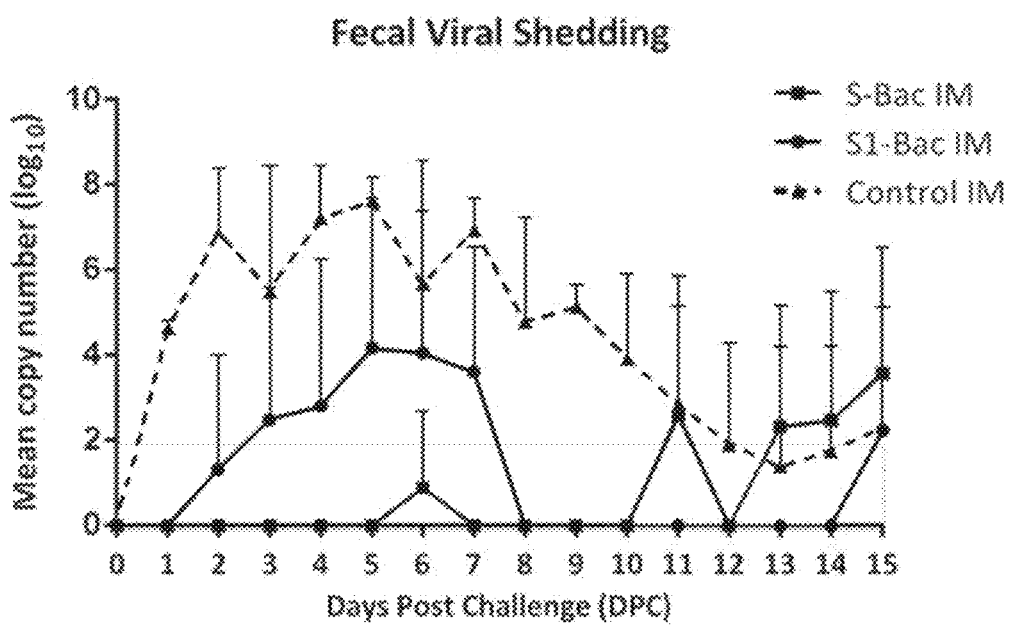
FIG. 11 shows the detection of fecal viral shedding after the high virulent porcine epidemic diarrhea virus (PEDV-PT) challenge. The detection limitation for this probe-based quantitative real-time RT PCR was 1.8 $\log^{10}$ and labeled as grey zone. The error bars represented the SD values of each group in different time points. The solid line with square icon and the gray line with round icon represent the average fecal viral shedding copy number of pigs in the S-Bac group and S1-Bac group, respectively. The average fecal viral shedding copy number of pigs in the control group was expressed as the dotted line with triangle icon.

The viral shedding of PEDV detected by a PEDV Nucleocapsid protein (N) sequence-based real-time RT PCR was present in FIG. 11. The pigs in the control group started to shed PEDVs into the stool with the mean value of the copy number of 4.6±0.19 $\log^{10}$ copies/mL at 1 DPC, continuously increased and fluctuated during 3 to 8 DPC with peak viral shedding of 7.6±0.57 $\log^{10}$ copies/mL at 5 DPC, and declined after 8 DPC. After 12 DPC, the amount of viral shedding in most of pigs in the control group was under the detection limit. In the S1-Bac immunized group, the virus started to be detected with the mean copy number of 2.5±3 $\log^{10}$ copies/mL at 3 DPC, lasted for 5 days with peak viral shedding of 4.2±3.5 $\log^{10}$ copies/mL at 5 DPC. Importantly, most pigs in the S-Bac group had no detectable viral shedding during 0-10 DPC, excepting 1 pig exhibited an intermittent viral shedding of 4.5 $\log^{10}$ copies/mL at 6 DPC and 7.7 $\log^{10}$ copies/mL at 11 DPC. Comparing with the control group, the amount of fecal viral shedding in the S-Bac group was statistically significantly lowered ($p<0.05$)

Figure 12:
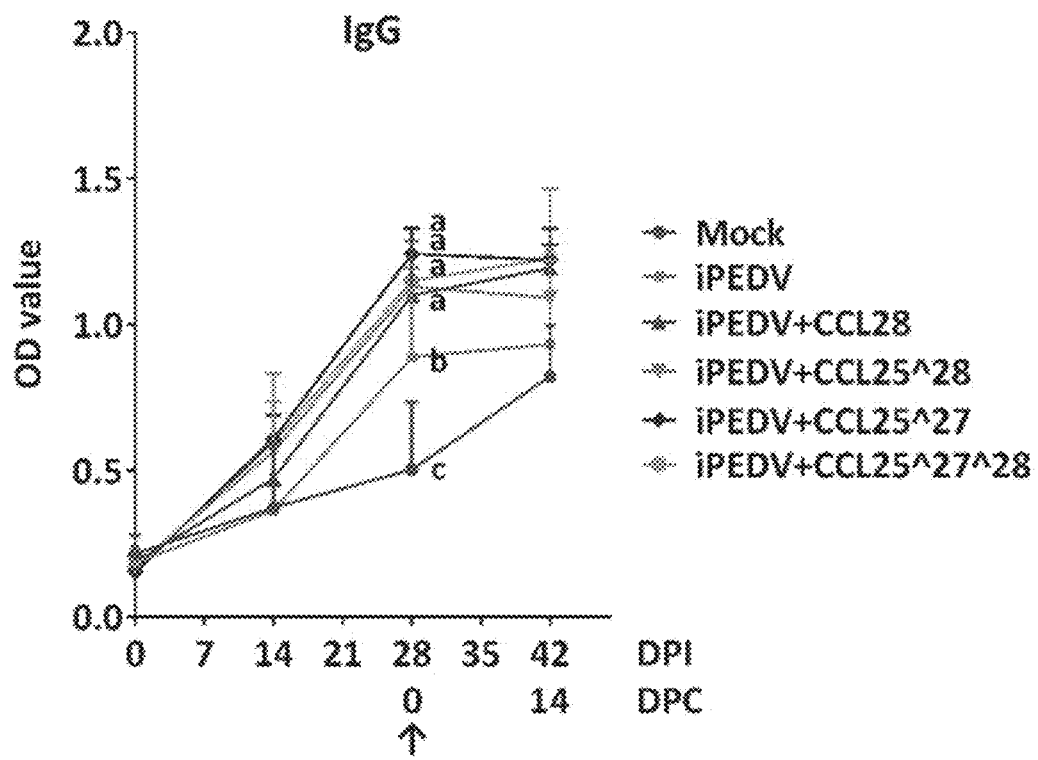
FIG. 12 shows the average optical density (OD) values of systemic IgG in each group with error bars represented the standard deviation (SD). The systemic PEDV spike-specific IgG in piglets at 0, 14, 28 days post-inoculation (DPI) and at 14 days post-challenge (DPC) following challenge with PEDVPT-P6&P7 were detected by an PEDV specific in-house ELISA. The arrow reflected the particular time (20 DPI or 0 DPC) of the PEDVPT-P6&P7 challenge. Statistically significant differences were demonstrated as a, b and c ($p<0.05$). DPI: day post inoculation; DPC: day post challenge
Figure 13:
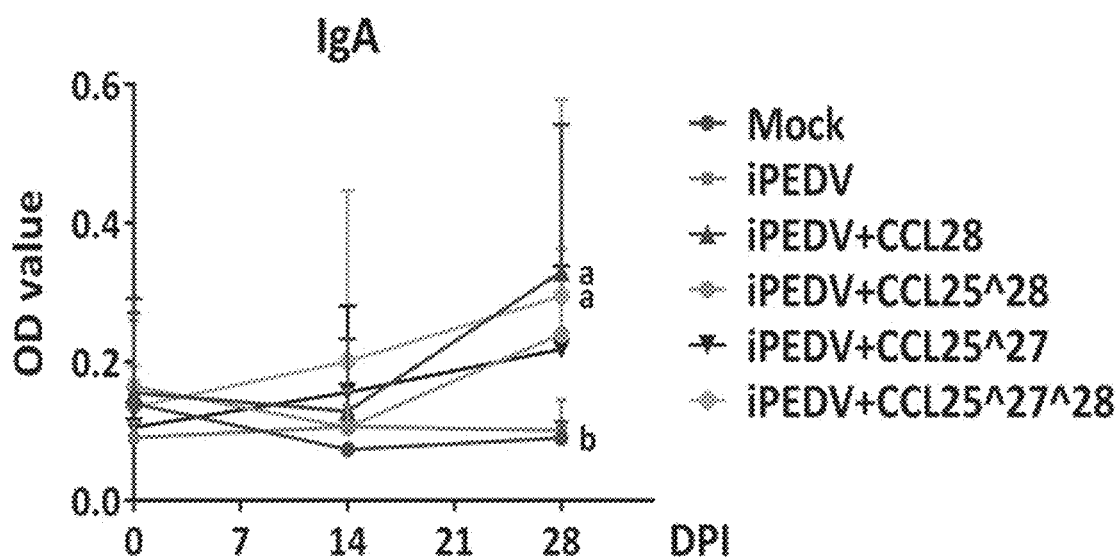
FIG. 13 shows the mean OD values of fecal IgA in each group of piglets.

Experiment 10: Chemokines (CCL27/CTACK, CCL28/MEK, and CCL25/TECK) as Immune Modulator The enhancement of PEDV specific systemic IgG and mucosal IgA in pigs intramuscularly immunized with CCL27/CTACK (SEQ ID NO: 09), CCL28/MEK (SEQ ID NO: 010), and/or CCL25/TECK (SEQ ID NO: 08) adjuvanted inactivated PEDV particles (iPEDV) were present in FIGS. 12 and 13, respectively. Compared to the mock and iPEDV group, immunization of piglets with iPEDV in combination with CCL28, both CCL25 and CCL28, both CCL25 and CCL27, or all CCL25, CCL27 and CCL28 could induce superior PEDV-specific IgG levels at 28 days post-inoculation (DPI) (FIG. 12). As to the PEDV-specific mucosal IgA, statistically significant increase of PEDV-specific IgA level was detected in iPEDV+CCL28 and iPEDV+CCL25^27^28 groups as compared to those of the mock group at 28 DPI (FIG. 13).

The specificity and sensitivity of antisera from experimentally infected piglets were examined using the insect cell-based ELISA. FIG. 14 shows the absorbance values of antibody produced in the PEDV virus infected piglets (upper panel) and the absorbance values of the sera collected from these piglets before PEDV infection. These results clearly demonstrated that this insect cell-based ELISA system has low background with high sensitivity against the PEDV-specific sera (FIG. 14).

What is claimed is:

1. A baculovirus displaying
porcine epidemic diarrhea virus S protein, or S1 domain of the S protein;
wherein the S protein comprises SEQ ID NO:1; and
wherein the S1 domain comprises SEQ ID NO:2.

2. A pharmaceutical composition comprising the baculovirus of claim 1 and a pharmaceutically acceptable carrier.

3. The pharmaceutical composition of claim 2, further comprising an adjuvant.

4. The pharmaceutical composition of claim 3, wherein said adjuvant comprises heat-labile enterotoxin B subunit (LTB), cholera toxin B (CTB), Chemokine (C-C motif) ligand 25, Chemokine (C-C motif) ligand 27, Chemokine (C-C motif) ligand 28, complete Freund's adjuvant, incomplete Freund's adjuvant, alumina gel, surfactant, anionic polymer, peptide, oily emulsion, or a combination thereof.

5. A method for evaluating porcine epidemic diarrhea virus infection, comprising: obtaining a sample from a subject to be evaluated; and contacting the sample with (1) a baculovirus displaying a protein comprising SEQ ID NO:1, SEQ ID NO:2, SEQ ID NO:5, or SEQ ID NO:6 or (2) an isolated cell comprising an expression cassette, said expression cassette comprising: a promoter and a polynucleotide encoding a protein comprising SEQ ID NO:1, SEQ ID NO:2, SEQ ID NO:5, or SEQ ID NO:6.

6. The method of claim 5, wherein the sample is a serum.

7. The method of claim 5, further comprising a step after the contacting step; wherein the step comprises detecting the interaction between the sample and the baculovirus or the sample and the cell.

8. A baculovirus displaying
(a) a first fusion comprising SEQ ID NO:5; or
(b) a second fusion protein comprising SEQ ID NO:6.

* * * * *

SEQUENCE LISTING

```
<160> NUMBER OF SEQ ID NOS: 14

<210> SEQ ID NO 1
<211> LENGTH: 1386
<212> TYPE: PRT
<213> ORGANISM: porcine epidemic diarrhea virus

<400> SEQUENCE: 1

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Lys Thr Asn Phe
            20                  25                  30

Arg Arg Phe Phe Ser Lys Phe Asn Val Gln Ala Pro Ala Val Val Val
        35                  40                  45
```

```
Leu Gly Gly Tyr Leu Pro Ile Gly Glu Asn Gln Gly Val Asn Ser Thr
     50                  55                  60

Trp Tyr Cys Ala Gly Gln His Pro Thr Ala Ser Gly Val His Gly Ile
 65                  70                  75                  80

Phe Val Ser His Ile Arg Gly Gly His Gly Phe Glu Ile Gly Ile Ser
                 85                  90                  95

Gln Glu Pro Phe Asp Pro Ser Gly Tyr Gln Leu Tyr Leu His Lys Ala
                100                 105                 110

Thr Asn Gly Asn Thr Asn Ala Thr Ala Arg Leu Arg Ile Cys Gln Phe
            115                 120                 125

Pro Ser Ile Lys Thr Leu Gly Pro Thr Ala Asn Asn Asp Val Thr Thr
        130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
450                 455                 460
```

```
Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
            485                 490                 495

Gln Pro Ile Ser Phe Val Thr Leu Pro Ser Phe Asn Asp His Ser Phe
        500                 505                 510

Val Asn Ile Thr Val Ser Ala Ser Phe Gly Gly His Ser Gly Ala Asn
    515                 520                 525

Leu Ile Ala Ser Asp Thr Thr Ile Asn Gly Phe Ser Ser Phe Cys Val
530                 535                 540

Asp Thr Arg Gln Phe Thr Ile Ser Leu Phe Tyr Asn Val Thr Asn Ser
545                 550                 555                 560

Tyr Gly Tyr Val Ser Asn Ser Gln Asp Ser Asn Cys Pro Phe Thr Leu
            565                 570                 575

Gln Ser Val Asn Asp Tyr Leu Ser Phe Ser Lys Phe Cys Val Ser Thr
        580                 585                 590

Ser Leu Leu Ala Ser Ala Cys Thr Ile Asp Leu Phe Gly Tyr Pro Glu
    595                 600                 605

Phe Gly Ser Gly Val Lys Phe Thr Ser Leu Tyr Phe Gln Phe Thr Lys
610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
            645                 650                 655

Phe Lys Gly Glu Gly Ile Ile Thr Leu Thr Asn Ser Ser Phe Leu Ala
        660                 665                 670

Gly Val Tyr Tyr Thr Ser Asp Ser Gly Gln Leu Leu Pro Phe Lys Asn
    675                 680                 685

Val Thr Ser Gly Ala Val Tyr Ser Val Thr Pro Cys Ser Phe Ser Glu
690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
            725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
    755                 760                 765

Ser Gly Gln Val Lys Ile Ala Pro Thr Val Thr Glu Asn Ile Ser Ile
770                 775                 780

Pro Thr Asn Phe Ser Met Ser Ile Lys Thr Glu Tyr Leu Gln Leu Tyr
785                 790                 795                 800

Asn Thr Pro Val Ser Val Asp Cys Ala Thr Tyr Val Cys Asn Gly Asn
            805                 810                 815

Ser Arg Cys Lys Gln Leu Leu Thr Gln Tyr Thr Ala Ala Cys Lys Thr
        820                 825                 830

Ile Glu Ser Ala Leu Gln Leu Ser Ala Arg Leu Glu Ser Val Glu Val
    835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
```

```
                885                 890                 895
Ile Glu Asp Leu Leu Phe Asn Lys Val Val Thr Asn Gly Leu Gly Thr
                900                 905                 910

Val Asp Glu Asp Tyr Lys Arg Cys Ser Asn Gly Arg Ser Val Ala Asp
                915                 920                 925

Leu Val Cys Ala Gln Tyr Tyr Ser Gly Val Met Val Leu Pro Gly Val
        930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Leu Pro Phe Ser Tyr
                965                 970                 975

Ala Val Gln Ala Arg Leu Asn Tyr Leu Ala Leu Gln Thr Asp Val Leu
                980                 985                 990

Gln Arg Asn Gln Gln Leu Leu Ala  Glu Ser Phe Asn Ser  Ala Ile Gly
            995                 1000                1005

Asn Ile  Thr Ser Ala Phe Glu  Ser Val Lys Glu Ala  Ile Ser Gln
        1010                1015                1020

Thr Ser  Lys Gly Leu Asn Thr  Val Ala His Ala Leu  Thr Lys Val
        1025                1030                1035

Gln Glu  Val Val Asn Ser Gln  Gly Ala Ala Leu Thr  Gln Leu Thr
        1040                1045                1050

Val Gln  Leu Gln His Asn Phe  Gln Ala Ile Ser Ser  Ser Ile Asp
        1055                1060                1065

Asp Ile  Tyr Ser Arg Leu Asp  Ile Leu Ser Ala Asp  Val Gln Val
        1070                1075                1080

Asp Arg  Leu Ile Thr Gly Arg  Leu Ser Ala Leu Asn  Ala Phe Val
        1085                1090                1095

Ala Gln  Thr Leu Thr Lys Tyr  Thr Glu Val Gln Ala  Ser Arg Lys
        1100                1105                1110

Leu Ala  Gln Gln Lys Val Asn  Glu Cys Val Lys Ser  Gln Ser Gln
        1115                1120                1125

Arg Tyr  Gly Phe Cys Gly Gly  Asp Gly Glu His Ile  Phe Ser Leu
        1130                1135                1140

Val Gln  Ala Ala Pro Gln Gly  Leu Leu Phe Leu His  Thr Val Leu
        1145                1150                1155

Val Pro  Ser Asp Phe Val Asp  Val Ile Ala Ile Ala  Gly Leu Cys
        1160                1165                1170

Val Asn  Asp Glu Ile Ala Leu  Thr Leu Arg Glu Pro  Gly Leu Val
        1175                1180                1185

Leu Phe  Thr His Glu Leu Gln  Asn His Thr Ala Thr  Glu Tyr Phe
        1190                1195                1200

Val Ser  Ser Arg Arg Met Phe  Glu Pro Arg Lys Pro  Thr Val Ser
        1205                1210                1215

Asp Phe  Val Gln Ile Glu Ser  Cys Val Val Thr Tyr  Val Asn Leu
        1220                1225                1230

Thr Arg  Asp Gln Leu Pro Asp  Val Ile Pro Asp Tyr  Ile Asp Val
        1235                1240                1245

Asn Lys  Thr Leu Asp Glu Ile  Leu Ala Ser Leu Pro  Asn Arg Thr
        1250                1255                1260

Gly Pro  Ser Leu Pro Leu Asp  Val Phe Asn Ala Thr  Tyr Leu Asn
        1265                1270                1275

Leu Thr  Gly Glu Ile Ala Asp  Leu Glu Gln Arg Ser  Glu Ser Leu
        1280                1285                1290
```

```
Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Ala Cys Phe Ser Gly Cys
    1355                1360                1365

Cys Arg Gly Pro Arg Leu Gln Pro Tyr Glu Val Phe Glu Lys Val
    1370                1375                1380

His Val Gln
    1385

<210> SEQ ID NO 2
<211> LENGTH: 737
<212> TYPE: PRT
<213> ORGANISM: porcine epidemic diarrhea virus

<400> SEQUENCE: 2

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Lys Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
```

```
                260                 265                 270
Val Val Ser Asn Gln Pro Leu Leu Val Asn Cys Leu Leu Ala Ile Pro
            275                 280                 285

Lys Ile Tyr Gly Leu Gly Gln Phe Phe Ser Phe Asn Gln Thr Ile Asp
290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
            355                 360                 365

Val Pro Tyr Tyr Cys Phe Leu Lys Val Asp Thr Tyr Asn Ser Thr Val
        370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
        450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
        530                 535                 540

Asp Thr Arg Gln Phe Thr Ile Ser Leu Phe Tyr Asn Val Thr Asn Ser
545                 550                 555                 560

Tyr Gly Tyr Val Ser Asn Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
            595                 600                 605

Phe Gly Ser Gly Val Lys Phe Thr Ser Leu Tyr Phe Gln Phe Thr Lys
        610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Pro Phe Lys Asn
            675                 680                 685
```

```
Val Thr Ser Gly Ala Val Tyr Ser Val Thr Pro Cys Ser Phe Ser Glu
690             695                 700

Gln Ala Ala Tyr Val Asp Asp Ile Val Gly Val Ile Ser Ser Leu
705             710                 715                 720

Ser Ser Ser Thr Phe Asn Ser Thr Arg Glu Leu Pro Gly Phe Phe Tyr
                725                 730                 735

His

<210> SEQ ID NO 3
<211> LENGTH: 440
<212> TYPE: PRT
<213> ORGANISM: porcine epidemic diarrhea virus

<400> SEQUENCE: 3

Ala Ser Val Ser Phe Gln Asp Arg Gly Arg Lys Arg Val Pro Leu Ser
1               5                   10                  15

Leu Tyr Ala Pro Leu Arg Val Thr Asn Asp Lys Pro Leu Ser Lys Val
                20                  25                  30

Leu Ala Asn Asn Ala Val Pro Thr Asn Lys Gly Asn Lys Asp Gln Gln
            35                  40                  45

Ile Gly Tyr Trp Asn Glu Gln Ile Arg Trp Arg Met Arg Arg Gly Glu
50              55                  60

Arg Ile Glu Gln Pro Ser Asn Trp His Phe Tyr Tyr Leu Gly Thr Gly
65              70                  75                  80

Pro His Ala Asp Leu Arg Tyr Arg Thr Arg Thr Glu Gly Val Phe Trp
                85                  90                  95

Val Ala Lys Glu Gly Ala Lys Thr Glu Pro Thr Asn Leu Gly Val Arg
                100                 105                 110

Lys Ala Ser Glu Lys Pro Ile Ile Pro Asn Phe Ser Gln Gln Leu Pro
            115                 120                 125

Ser Val Val Glu Ile Val Glu Pro Asn Thr Pro Pro Thr Ser Arg Ala
130                 135                 140

Asn Ser Arg Ser Arg Ser Arg Gly Asn Gly Asn Asn Arg Ser Arg Ser
145                 150                 155                 160

Pro Ser Asn Asn Arg Gly Asn Asn Gln Ser Arg Gly Asn Ser Gln Asn
                165                 170                 175

Arg Gly Asn Asn Gln Gly Arg Gly Ala Ser Gln Asn Arg Gly Gly Asn
                180                 185                 190

Asn Asn Asn Asn Lys Ser Arg Asn Gln Ser Lys Asn Arg Asn Gln
            195                 200                 205

Ser Asn Asp Arg Gly Gly Val Thr Ser Arg Asp Asp Leu Val Ala Ala
210                 215                 220

Val Lys Asp Ala Leu Lys Ser Leu Gly Ile Gly Glu Asn Pro Asp Lys
225                 230                 235                 240

Leu Lys Gln Gln Gln Lys Pro Lys Gln Glu Arg Ser Asp Ser Ser Gly
                245                 250                 255

Lys Asn Thr Pro Lys Lys Asn Lys Ser Arg Ala Thr Ser Lys Glu Arg
            260                 265                 270

Asp Leu Lys Asp Ile Pro Glu Trp Arg Arg Ile Pro Lys Gly Glu Asn
                275                 280                 285

Ser Val Ala Ala Cys Phe Gly Pro Arg Gly Gly Phe Lys Asn Phe Gly
290                 295                 300

Asp Ala Glu Phe Val Glu Lys Gly Val Asp Ala Ser Gly Tyr Ala Gln
305                 310                 315                 320
```

```
Ile Ala Ser Leu Ala Pro Asn Val Ala Leu Leu Phe Gly Gly Asn
            325                 330                 335

Val Ala Val Arg Glu Leu Ala Asp Ser Tyr Glu Ile Thr Tyr Asn Tyr
        340                 345                 350

Lys Met Thr Val Pro Lys Ser Asp Pro Asn Val Glu Leu Leu Val Ser
            355                 360                 365

Gln Val Asp Ala Phe Lys Thr Gly Asn Ala Lys Pro Gln Arg Lys Lys
        370                 375                 380

Glu Lys Lys Asn Lys Arg Glu Thr Thr Gln Gln Leu Asn Glu Glu Ala
385                 390                 395                 400

Ile Tyr Asp Asp Val Gly Val Pro Ser Asp Val Thr His Ala Asn Leu
            405                 410                 415

Glu Trp Asp Thr Ala Val Asp Gly Gly Asp Thr Ala Val Glu Ile Ile
            420                 425                 430

Asn Glu Ile Phe Asp Thr Gly Asn
            435                 440

<210> SEQ ID NO 4
<211> LENGTH: 30
<212> TYPE: PRT
<213> ORGANISM: baculovirus

<400> SEQUENCE: 4

Phe Met Phe Gly His Val Val Asn Phe Val Ile Ile Leu Ile Val Ile
1               5                   10                  15

Leu Phe Leu Tyr Cys Met Ile Arg Asn Arg Asn Arg Gln Tyr
            20                  25                  30

<210> SEQ ID NO 5
<211> LENGTH: 1416
<212> TYPE: PRT
<213> ORGANISM: Artificial Sequence
<220> FEATURE:
<223> OTHER INFORMATION: fusion protein

<400> SEQUENCE: 5

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Lys Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160
```

-continued

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Asn Ser Gln Asp Ser Asn Cys Pro Phe Thr Leu
                565                 570                 575

Gln Ser Val Asn Asp Tyr Leu Ser Phe Ser Lys Phe Cys Val Ser Thr

```
            580             585             590
Ser Leu Leu Ala Ser Ala Cys Thr Ile Asp Leu Phe Gly Tyr Pro Glu
            595             600             605

Phe Gly Ser Gly Val Lys Phe Thr Ser Leu Tyr Phe Gln Phe Thr Lys
            610             615             620

Gly Glu Leu Ile Thr Gly Thr Pro Lys Pro Leu Glu Gly Val Thr Asp
625             630             635             640

Val Ser Phe Met Thr Leu Asp Val Cys Thr Lys Tyr Thr Ile Tyr Gly
                645             650             655

Phe Lys Gly Glu Gly Ile Ile Thr Leu Thr Asn Ser Ser Phe Leu Ala
            660             665             670

Gly Val Tyr Tyr Thr Ser Asp Ser Gly Gln Leu Leu Pro Phe Lys Asn
            675             680             685

Val Thr Ser Gly Ala Val Tyr Ser Val Thr Pro Cys Ser Phe Ser Glu
            690             695             700

Gln Ala Ala Tyr Val Asp Asp Ile Val Gly Val Ile Ser Ser Leu
705             710             715             720

Ser Ser Ser Thr Phe Asn Ser Thr Arg Glu Leu Pro Gly Phe Phe Tyr
                725             730             735

His Ser Asn Asp Gly Ser Asn Cys Thr Glu Pro Val Leu Val Tyr Ser
                740             745             750

Asn Ile Gly Val Cys Lys Ser Gly Ser Ile Gly Tyr Val Pro Ser Gln
            755             760             765

Ser Gly Gln Val Lys Ile Ala Pro Thr Val Thr Glu Asn Ile Ser Ile
            770             775             780

Pro Thr Asn Phe Ser Met Ser Ile Lys Thr Glu Tyr Leu Gln Leu Tyr
785             790             795             800

Asn Thr Pro Val Ser Val Asp Cys Ala Thr Tyr Val Cys Asn Gly Asn
                805             810             815

Ser Arg Cys Lys Gln Leu Leu Thr Gln Tyr Thr Ala Ala Cys Lys Thr
                820             825             830

Ile Glu Ser Ala Leu Gln Leu Ser Ala Arg Leu Glu Ser Val Glu Val
                835             840             845

Asn Ser Met Leu Thr Ile Ser Glu Glu Ala Leu Gln Leu Ala Thr Ile
850             855             860

Ser Ser Phe Asn Gly Asp Gly Tyr Asn Phe Thr Asn Val Leu Gly Val
865             870             875             880

Ser Val Tyr Asp Pro Ala Ser Gly Arg Val Val Gln Lys Arg Ser Phe
            885             890             895

Ile Glu Asp Leu Leu Phe Asn Lys Val Val Thr Asn Gly Leu Gly Thr
            900             905             910

Val Asp Glu Asp Tyr Lys Arg Cys Ser Asn Gly Arg Ser Val Ala Asp
            915             920             925

Leu Val Cys Ala Gln Tyr Tyr Ser Gly Val Met Val Leu Pro Gly Val
            930             935             940

Val Asp Ala Glu Lys Leu His Met Tyr Ser Ala Ser Leu Ile Gly Gly
945             950             955             960

Met Val Leu Gly Gly Phe Thr Ala Ala Leu Pro Phe Ser Tyr
                965             970             975

Ala Val Gln Ala Arg Leu Asn Tyr Leu Ala Leu Gln Thr Asp Val Leu
            980             985             990

Gln Arg Asn Gln Gln Leu Leu Ala  Glu Ser Phe Asn Ser  Ala Ile Gly
            995             1000            1005
```

```
Asn Ile Thr Ser Ala Phe Glu Ser Val Lys Glu Ala Ile Ser Gln
    1010            1015            1020

Thr Ser Lys Gly Leu Asn Thr Val Ala His Ala Leu Thr Lys Val
    1025            1030            1035

Gln Glu Val Val Asn Ser Gly Ala Ala Leu Thr Gln Leu Thr
    1040            1045            1050

Val Gln Leu Gln His Asn Phe Gln Ala Ile Ser Ser Ile Asp
    1055            1060            1065

Asp Ile Tyr Ser Arg Leu Asp Ile Leu Ser Ala Asp Val Gln Val
    1070            1075            1080

Asp Arg Leu Ile Thr Gly Arg Leu Ser Ala Leu Asn Ala Phe Val
    1085            1090            1095

Ala Gln Thr Leu Thr Lys Tyr Thr Glu Val Gln Ala Ser Arg Lys
    1100            1105            1110

Leu Ala Gln Gln Lys Val Asn Glu Cys Val Lys Ser Gln Ser Gln
    1115            1120            1125

Arg Tyr Gly Phe Cys Gly Gly Asp Gly Glu His Ile Phe Ser Leu
    1130            1135            1140

Val Gln Ala Ala Pro Gln Gly Leu Leu Phe Leu His Thr Val Leu
    1145            1150            1155

Val Pro Ser Asp Phe Val Asp Val Ile Ala Ile Ala Gly Leu Cys
    1160            1165            1170

Val Asn Asp Glu Ile Ala Leu Thr Leu Arg Glu Pro Gly Leu Val
    1175            1180            1185

Leu Phe Thr His Glu Leu Gln Asn His Thr Ala Thr Glu Tyr Phe
    1190            1195            1200

Val Ser Ser Arg Arg Met Phe Glu Pro Arg Lys Pro Thr Val Ser
    1205            1210            1215

Asp Phe Val Gln Ile Glu Ser Cys Val Val Thr Tyr Val Asn Leu
    1220            1225            1230

Thr Arg Asp Gln Leu Pro Asp Val Ile Pro Asp Tyr Ile Asp Val
    1235            1240            1245

Asn Lys Thr Leu Asp Glu Ile Leu Ala Ser Leu Pro Asn Arg Thr
    1250            1255            1260

Gly Pro Ser Leu Pro Leu Asp Val Phe Asn Ala Thr Tyr Leu Asn
    1265            1270            1275

Leu Thr Gly Glu Ile Ala Asp Leu Glu Gln Arg Ser Glu Ser Leu
    1280            1285            1290

Arg Asn Thr Thr Glu Glu Leu Gln Ser Leu Ile Tyr Asn Ile Asn
    1295            1300            1305

Asn Thr Leu Val Asp Leu Glu Trp Leu Asn Arg Val Glu Thr Tyr
    1310            1315            1320

Ile Lys Trp Pro Trp Trp Val Trp Leu Ile Ile Phe Ile Val Leu
    1325            1330            1335

Ile Phe Val Val Ser Leu Leu Val Phe Cys Cys Ile Ser Thr Gly
    1340            1345            1350

Cys Cys Gly Cys Cys Gly Cys Cys Ala Cys Phe Ser Gly Cys
    1355            1360            1365

Cys Arg Gly Pro Arg Leu Gln Pro Tyr Glu Val Phe Glu Lys Val
    1370            1375            1380

His Val Gln Phe Met Phe Gly His Val Val Asn Phe Val Ile Ile
    1385            1390            1395
```

```
Leu Ile Val Ile Leu Phe Leu Tyr Cys Met Ile Arg Asn Arg Asn
    1400                1405                1410

Arg Gln Tyr
    1415

<210> SEQ ID NO 6
<211> LENGTH: 767
<212> TYPE: PRT
<213> ORGANISM: Artificial Sequence
<220> FEATURE:
<223> OTHER INFORMATION: fusion protein

<400> SEQUENCE: 6

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Lys Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335
```

```
Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
    355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
            435                 440                 445

Ala Leu Ile Glu Val Gln Gly Thr Ala Ile Gln Arg Ile Leu Tyr Cys
            450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
            530                 535                 540

Asp Thr Arg Gln Phe Thr Ile Ser Leu Phe Tyr Asn Val Thr Asn Ser
545                 550                 555                 560

Tyr Gly Tyr Val Ser Asn Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
            595                 600                 605

Phe Gly Ser Gly Val Lys Phe Thr Ser Leu Tyr Phe Gln Phe Thr Lys
            610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Val Tyr Tyr Thr Ser Asp Ser Gly Gln Leu Leu Pro Phe Lys Asn
            675                 680                 685

Val Thr Ser Gly Ala Val Tyr Ser Val Thr Pro Cys Ser Phe Ser Glu
            690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Phe Met Phe Gly His Val Val Asn Phe Val Ile Ile Leu Ile Val
                740                 745                 750

Ile Leu Phe Leu Tyr Cys Met Ile Arg Asn Arg Asn Arg Gln Tyr
```

<210> SEQ ID NO 7
<211> LENGTH: 470
<212> TYPE: PRT
<213> ORGANISM: Artificial Sequence
<220> FEATURE:
<223> OTHER INFORMATION: fusion protein

<400> SEQUENCE: 7

```
Ala Ser Val Ser Phe Gln Asp Arg Gly Arg Lys Arg Val Pro Leu Ser
1               5                   10                  15

Leu Tyr Ala Pro Leu Arg Val Thr Asn Asp Lys Pro Leu Ser Lys Val
            20                  25                  30

Leu Ala Asn Asn Ala Val Pro Thr Asn Lys Gly Asn Lys Asp Gln Gln
        35                  40                  45

Ile Gly Tyr Trp Asn Glu Gln Ile Arg Trp Arg Met Arg Arg Gly Glu
    50                  55                  60

Arg Ile Glu Gln Pro Ser Asn Trp His Phe Tyr Tyr Leu Gly Thr Gly
65                  70                  75                  80

Pro His Ala Asp Leu Arg Tyr Arg Thr Arg Thr Glu Gly Val Phe Trp
                85                  90                  95

Val Ala Lys Glu Gly Ala Lys Thr Glu Pro Thr Asn Leu Gly Val Arg
            100                 105                 110

Lys Ala Ser Glu Lys Pro Ile Ile Pro Asn Phe Ser Gln Gln Leu Pro
        115                 120                 125

Ser Val Val Glu Ile Val Glu Pro Asn Thr Pro Thr Ser Arg Ala
    130                 135                 140

Asn Ser Arg Ser Arg Ser Arg Gly Asn Gly Asn Asn Arg Ser Arg Ser
145                 150                 155                 160

Pro Ser Asn Asn Arg Gly Asn Asn Gln Ser Arg Gly Asn Ser Gln Asn
                165                 170                 175

Arg Gly Asn Asn Gln Gly Arg Gly Ala Ser Gln Asn Arg Gly Gly Asn
            180                 185                 190

Asn Asn Asn Asn Lys Ser Arg Asn Gln Ser Lys Asn Arg Asn Gln
        195                 200                 205

Ser Asn Asp Arg Gly Gly Val Thr Ser Arg Asp Asp Leu Val Ala Ala
    210                 215                 220

Val Lys Asp Ala Leu Lys Ser Leu Gly Ile Gly Glu Asn Pro Asp Lys
225                 230                 235                 240

Leu Lys Gln Gln Gln Lys Pro Lys Gln Glu Arg Ser Asp Ser Ser Gly
                245                 250                 255

Lys Asn Thr Pro Lys Lys Asn Lys Ser Arg Ala Thr Ser Lys Glu Arg
            260                 265                 270

Asp Leu Lys Asp Ile Pro Glu Trp Arg Arg Ile Pro Lys Gly Glu Asn
        275                 280                 285

Ser Val Ala Ala Cys Phe Gly Pro Arg Gly Gly Phe Lys Asn Phe Gly
    290                 295                 300

Asp Ala Glu Phe Val Glu Lys Gly Val Asp Ala Ser Gly Tyr Ala Gln
305                 310                 315                 320

Ile Ala Ser Leu Ala Pro Asn Val Ala Ala Leu Leu Phe Gly Gly Asn
                325                 330                 335

Val Ala Val Arg Glu Leu Ala Asp Ser Tyr Glu Ile Thr Tyr Asn Tyr
            340                 345                 350

Lys Met Thr Val Pro Lys Ser Asp Pro Asn Val Glu Leu Leu Val Ser
```

```
                355                 360                 365
Gln Val Asp Ala Phe Lys Thr Gly Asn Ala Lys Pro Gln Arg Lys Lys
    370                 375                 380

Glu Lys Lys Asn Lys Arg Glu Thr Thr Gln Gln Leu Asn Glu Glu Ala
385                 390                 395                 400

Ile Tyr Asp Asp Val Gly Val Pro Ser Asp Val Thr His Ala Asn Leu
                405                 410                 415

Glu Trp Asp Thr Ala Val Asp Gly Gly Asp Thr Ala Val Glu Ile Ile
            420                 425                 430

Asn Glu Ile Phe Asp Thr Gly Asn Phe Met Phe Gly His Val Val Asn
                435                 440                 445

Phe Val Ile Ile Leu Ile Val Ile Leu Phe Leu Tyr Cys Met Ile Arg
    450                 455                 460

Asn Arg Asn Arg Gln Tyr
465                 470

<210> SEQ ID NO 8
<211> LENGTH: 186
<212> TYPE: PRT
<213> ORGANISM: Sus scrofa

<400> SEQUENCE: 8

Met Arg Pro Trp Leu Leu Ala Cys Leu Val Ala Cys Phe Val Gly Ala
1               5                   10                  15

Trp Ala Pro Ala Ile His Ala Gln Gly Ala Phe Glu Asp Cys Cys Leu
                20                  25                  30

Ala Tyr His Ser His Ile Lys Trp Arg Leu Leu Arg Arg Ala His Ser
            35                  40                  45

Tyr Gln Arg Gln Asp Val Ser Gly Ser Cys Asn Leu Pro Ala Val Ile
        50                  55                  60

Phe Phe Phe Pro Gln Lys Asp Lys Met Val Cys Gly Lys Pro Gly Ala
65                  70                  75                  80

Lys Trp Val Gln Phe Gly Met Lys Ile Leu Asp Asn Arg Asn Lys Lys
                85                  90                  95

Asp Ser Lys Pro His His Ser Gly Arg Arg Phe Gln Gly Pro Gln
                100                 105                 110

Ser Gly Val Arg Lys Leu Ser Ser Gly Thr Ser Arg Pro Leu Leu Leu
            115                 120                 125

Lys Phe Ser Gly Pro Thr Arg Ser Ser Lys Arg Lys Ala Ser Leu Leu
        130                 135                 140

Thr Thr Ala Ile Pro Gly Pro Arg Gly Arg Ser Ser Leu Glu Gly Pro
145                 150                 155                 160

Arg Phe Glu Gly Lys Pro Ile Pro Asn Pro Leu Leu Gly Leu Asp Ser
                165                 170                 175

Thr Arg Thr Gly His His His His His His
            180                 185

<210> SEQ ID NO 9
<211> LENGTH: 143
<212> TYPE: PRT
<213> ORGANISM: Sus scrofa

<400> SEQUENCE: 9

Met Lys Gly Pro Ser Pro Thr Ser Ser Leu Leu Leu Ile Leu Leu Leu
1               5                   10                  15

Leu Ser Pro Asp Pro Gly Ala Ala Leu Ile Leu Pro Pro Ser Thr Thr
```

```
            20                  25                  30
Cys Cys Thr Gln Leu Tyr Arg Gln Pro Leu Ser Ser Lys Leu Leu Arg
        35                  40                  45

Gln Ile Ile Arg Val Glu Leu Gln Glu Ala Asp Gly Asp Cys His Leu
 50                  55                  60

Gln Ala Phe Val Leu His Leu Ser Arg Arg Ser Val Cys Ile His Pro
 65                  70                  75                  80

Gln Asn Arg Ser Leu Ala Arg Trp Phe Glu His His Gly Arg Arg Leu
                85                  90                  95

Gln Gly Thr Leu Pro Lys Leu Ser Leu Gly Leu Arg Gly Arg Ser Ser
            100                 105                 110

Leu Glu Gly Pro Arg Phe Glu Gly Lys Pro Ile Pro Asn Pro Leu Leu
        115                 120                 125

Gly Leu Asp Ser Thr Arg Thr Gly His His His His His Glu
        130                 135                 140

<210> SEQ ID NO 10
<211> LENGTH: 162
<212> TYPE: PRT
<213> ORGANISM: Sus scrofa

<400> SEQUENCE: 10

Met Gln His Thr Gly Leu Ala Leu Val Ala Leu Ala Ala Cys Val Ala
 1               5                  10                  15

Leu His His Ser Glu Ala Ile Leu Pro Ile Ala Ser Ser Cys Cys Thr
                20                  25                  30

Glu Val Ser His His Ile Ser Arg Arg Leu Leu Glu Arg Val Asn Thr
            35                  40                  45

Cys Arg Leu Gln Arg Ala Asp Gly Asp Cys Asp Leu Ala Ala Val Ile
 50                  55                  60

Leu His Val Lys Arg Arg Ile Cys Val Ser Pro His Asn His Leu
 65                  70                  75                  80

Ile Lys Gln Trp Met Lys Glu Gln Ala Ala Lys Lys Asp Ala Lys Gly
                85                  90                  95

Asn Ile Cys His Lys Lys Lys His Ser Lys Arg Asn Ser Lys Gly
            100                 105                 110

Ala His Gln Glu Lys His Glu Thr His Gly His Lys Thr Pro Tyr Arg
        115                 120                 125

Gly Arg Ser Ser Leu Glu Gly Pro Arg Phe Glu Gly Lys Pro Ile Pro
        130                 135                 140

Asn Pro Leu Leu Gly Leu Asp Ser Thr Arg Thr Gly His His His
145                 150                 155                 160

His His

<210> SEQ ID NO 11
<211> LENGTH: 5238
<212> TYPE: DNA
<213> ORGANISM: Artificial Sequence
<220> FEATURE:
<223> OTHER INFORMATION: cassette

<400> SEQUENCE: 11
tcctgcatct ttaatcaaa tcccaagatg tgtataaacg cgccggtatg tacaggaaga       60
ggtttatact aaactgttac attgcaaacg tggtttcgtg tgccaagtgt gaaaaccgat     120
gtttaatcaa ggctctgacg catttctaca accacgactc caagtgtgtg ggtgaagtca     180
```

```
tgcatctttt aatcaaatcc caagatgtgt ataaaccacc aaactgccaa aaatgaaaa      240 ctgtcgacaa gctctgtccg tttgctggca actgcaaggg tctcaatcct atttgtaatt     300
attgaataat aaaacaatta taaatgtcaa atttgttttt tattaacgat acaaaccaaa     360
cgcaacaaga acatttgtag tattatctat aattgaaaac gcgtagttat aatcgctgag     420
gtaatattta aaatcatttt caatgattc acagttaatt tgcgacaata taatttatt      480 ttcacataaa ctagacgcct tgtcgtcttc ttcttcgtat tccttctctt tttcattttt     540
ctcttcataa aaattaacat agttattatc gtatccatat atgtatctat cgtatagagt     600
aaattttttg ttgtcataaa tatatatgtc ttttttaatg gggtgtatag taccgctgcg     660
catagttttt ctgtaattta caacagtgct attttctggt agttcttcgg agtgtgttgc     720
tttaattatt aaatttatat aatcaatgaa tttgggatcg tcggttttgt acaatatgtt     780
gccggcatag tacgcagctt cttctagttc aattacacca ttttttagca gcaccggatt     840
aacataactt tccaaaatgt tgtacgaacc gttaaacaaa acagttcac ctcccttttc      900 tatactattg tctgcgagca gttgtttgtt gttaaaaata acagccattg taatgagacg     960
cacaaactaa tatcacaaac tggaaatgtc tatcaatata tagttgctga tggccggcct    1020
attaatagta atcaattacg gggtcattag ttcatagccc atatatggag ttccgcgtta    1080
cataacttac ggtaaatggc ccgcctggct gaccgcccaa cgaccccgc ccattgacgt      1140 caataatgac gtatgttccc atagtaacgc caataggac tttccattga cgtcaatggg     1200
tggagtattt acggtaaact gcccacttgg cagtacatca agtgtatcat atgccaagtc    1260
cgccccctat tgacgtcaat gacggtaaat ggcccgcctg gcattatgcc cagtacatga    1320
ccttacggga cttttcctact tggcagtaca tctacgtatt agtcatcgct attaccatgc    1380
tgatgcggtt ttggcagtac accaatgggc gtggatagcg gtttgactca cggggatttc    1440
caagtctcca ccccattgac gtcaatggga gtttgttttg gcaccaaaat caacgggact    1500
ttccaaaatg tcgtaataac cccgccccgt tgacgcaaat gggcggtagg cgtgtacggt    1560
gggaggtcta tataagcaga cgtcgtttag tgaaccgtca gatcactaga tgctttattg    1620
cggtagttta tcacagttaa attgctaacg ccagtctcga acttaacgtg cagaagttgg    1680
tcgtgaggca ctgggcaggt aagtatcggg ccctttgtgc gggggggagcg gctcggggct    1740 gtccgcgggg ggacggctgc cttcgggggg gacggggcag ggcggggttc ggcttctggc    1800
gtgtgaccgg cggctctaga gcctctgcta accatgttca tgccttcttc ttttttcctac    1860 agctcctggg caacgtgctg gttattgtgc tgtctcatca ttttggcaaa gaattggatc    1920
ggaccgaaat taatacgact cactataggg gaattgtgag cggataacaa ttccccggag    1980
ttaatccggg acctttaatt caacccaaca caatatatta tagttaaata agaattatta    2040
tcaaatcatt tgtatattaa ttaaaatact atactgtaaa ttcattttta tttacaatca    2100
aaggagatat accatggcac accatcacca ccatcactct tctggtaaag aaaccgctgc    2160
tgcgaaattt gaacgccagc acatggactc gccaccgcct tctggtctgg tccccgggg     2220 cagcgcaggt tctggtacga ttgatgacga cgacaagagt ccgggcttct cctcaacgat    2280
atctgagctc gtggatccga attctcagat ctcggcgcgc ctgcaggtcg acggtaccgg    2340
ttcgaagctt gcggccgcac agctgtatac acgtgcaagc cagccagaac tcgccccgga    2400 agacccgag gatctcgagc accaccatca ccatcaccat cactaagtga ttaacctcag     2460
gtgcaggctg cctatcagaa ggtggtggct ggtgtggcca atgccctggc tcacaaatac    2520
cactgagatc gatctttttc cctctgccaa aaattatggg gacatcatga agccccttga    2580
```

```
gcatctgact tctggctaat aaaggaaatt tattttcatt gcaatagtgt gttggaattt    2640
tttgtgtctc tcactcggaa ggacatatgg gagggcaaat catttaaaac atcagaatga    2700
gtatttggtt tagagtttgg caacatatgc ccatatgtaa ctagcataac cccttggggc    2760
ctctaaacgg gtcttgaggg gttttttgct gaaagcatgc ggaggaaatt ctccttgaag    2820
tttccctggt gttcaaagta aaggagtttg caccagacgc acctctgttc actggtccgg    2880
cgtattaaaa cacgatacat tgttattagt acatttatta agcgctagat tctgtgcgtt    2940
gttgatttac agacaattgt tgtacgtatt ttaataattc attaaattta taatctttag    3000
ggtggtatgt tagagcgaaa atcaaatgat tttcagcgtc tttatatctg aatttaaata    3060
ttaaatcctc aatagatttg taaaataggt ttcgattagt ttcaaacaag ggttgttttt    3120
ccgaaccgat ggctggacta tctaatggat tttcgctcaa cgccacaaaa cttgccaaat    3180
cttgtagcag caatctagct ttgtcgatat tcgtttgtgt tttgttttgt aataaaggtt    3240
cgacgtcgtt caaatatatta tgcgcttttg tatttctttc atcactgtcg ttagtgtaca    3300
attgactcga cgtaaacacg ttaaatagag cttggacata tttaacatcg ggcgtgttag    3360
ctttattagg ccgattatcg tcgtcgtccc aaccctcgtc gttagaagtt gcttccgaag    3420
acgattttgc catagccaca cgacgcctat taattgtgtc ggctaacacg tccgcgatca    3480
aatttgtagt tgagcttttt ggaattgcga tcgcataact tcgtatagca tacattatac    3540
gaagttataa gctcggaacg ctgcgctcgg tcgttcggct gcggcgagcg gtatcagctc    3600
actcaaaggc ggtaatacgg ttatccacag aatcagggga taacgcagga aagaacatgt    3660
gagcaaaagg ccagcaaaag gccaggaacc gtaaaaaggc cgcgttgctg gcgttttttcc    3720 ataggctccg ccccctgacg agcatcacaa aaatcgacgc tcaagtcaga ggtggcgaaa    3780
cccgacagga ctataaagat accaggcgtt tcccctgga agctccctcg tgcgctctcc    3840
tgttccgacc ctgccgctta ccggatacct gtccgccttt ctcccttcgg gaagcgtggc    3900
gctttctcaa tgctcacgct gtaggtatct cagttcggtg taggtcgttc gctccaagct    3960
gggctgtgtg cacgaacccc ccgttcagcc cgaccgctgc gccttatccg gtaactatcg    4020
tcttgagtcc aacccggtaa gacacgactt atcgccactg gcagcagcca ctggtaacag    4080
gattagcaga gcgaggtatg taggcggtgc tacagagttc ttgaagtggt ggcctaacta    4140
cggctacact agaagaacag tatttggtat ctgcgctctg ctgaagccag ttaccttcgg    4200
aaaaagagtt ggtagctctt gatccggcaa acaaaccacc gctggtagcg gtggtttttt    4260
tgtttgcaag cagcagatta cgcgcagaaa aaaggatct caagaagatc ctttgttacc    4320
aatgcttaat cagtgaggca cctatctcag cgatctgtct atttcgttca tccatagttg    4380
cctgactccc cgtcgtgtag ataactacga tacgggaggg cttaccatct ggccccagtg    4440
ctgcaatgat accgcgagac ccacgctcac cggctccaga tttatcagca ataaaccagc    4500
cagccggaag ggccgagcgc agaagtggtc ctgcaacttt atccgcctcc atccagtcta    4560
ttaattgttg ccgggaagct agagtaagta gttcgccagt taatagtttg cgcaacgttg    4620
ttgccattgc tacaggcatc gtggtgtcac gctcgtcgtt tggtatggct tcattcagct    4680
ccggttccca acgatcaagg cgagttacat gatcccccat gttgtgcaaa aaagcggtta    4740
gctccttcgg tcctccgatc gttgtcagaa gtaagttggc cgcagtgtta tcactcatgg    4800
ttatggcagc actgcataat tctcttactg tcatgccatc cgtaagatgc ttttctgtga    4860
ctggtgagta ctcaaccaag tcattctgag aatagtgtat gcggcgaccg agttgctctt    4920
```

```
gcccggcgtc aatacgggat aataccgcgc cacatagcag aactttaaaa gtgctcatca    4980
ttggaaaacg ttcttcgggg cgaaaactct caaggatctt accgctgttg agatccagtt    5040
cgatgtaacc cactcgtgca cccaactgat cttcagcatc ttttactttc accagcgttt    5100
ctgggtgagc aaaaacagga aggcaaaatg ccgcaaaaaa gggaataagg gcgacacgga    5160
aatgttgaat actcatactc ttccttttc  aatattattg aagcatttat cagggttatt    5220
gtctcatgtc cgcgcgtt                                                  5238

<210> SEQ ID NO 12
<211> LENGTH: 24
<212> TYPE: DNA
<213> ORGANISM: Artificial Sequence
<220> FEATURE:
<223> OTHER INFORMATION: probe

<400> SEQUENCE: 12
tgyyaccayy accacgactc ctgc                                           24

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
cgcaaagact gaacccacta ac                                             22

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
ttgcctctgt tgttacttgg agat                                           24
```